(12) United States Patent
Al Najjar et al.

(10) Patent No.: US 10,682,250 B1
(45) Date of Patent: Jun. 16, 2020

(54) ROBOTIC GRIPPING ASSIST

(71) Applicant: UNITED ARAB EMIRATES UNIVERSITY, Al Ain (AE)

(72) Inventors: Fady Al Najjar, Al Ain (AE); Nouf Fadel Nasser Alsaedi, Al Ain (AE); Waleed Khalil Ahmed, Al Ain (AE); Mostafa Al Kasabi, Al Ain (AE)

(73) Assignee: United Arab Emirated University, Al-Ain (AE)

( * ) Notice: Subject to any disclaimer, the term of this patent is extended or adjusted under 35 U.S.C. 154(b) by 0 days.

(21) Appl. No.: 16/572,538

(22) Filed: Sep. 16, 2019

Related U.S. Application Data

(63) Continuation-in-part of application No. 16/351,458, filed on Mar. 12, 2019, now Pat. No. 10,449,677.

(51) Int. Cl.
  *A61F 5/01* (2006.01)
  *B25J 9/00* (2006.01)

(52) U.S. Cl.
  CPC ............ *A61F 5/013* (2013.01); *B25J 9/0006* (2013.01); *B25J 9/0015* (2013.01); *A61F 2005/0155* (2013.01); *A61H 2201/14* (2013.01); *A61H 2201/1638* (2013.01)

(58) Field of Classification Search
  CPC ... A61F 5/013; A61F 2005/0155; A61H 1/00; A61H 1/02; A61H 1/0285; A61H 1/0288; A61H 2201/14; A61H 2201/1638; B25J 9/0006; B25J 9/0015
  USPC ................................................ 601/5, 33, 40
  See application file for complete search history.

(56) References Cited

U.S. PATENT DOCUMENTS

| | | | | |
|---|---|---|---|---|
| 10,449,677 | B1* | 10/2019 | Al Najjar | B25J 13/085 |
| 2003/0073939 | A1* | 4/2003 | Taylor | A61H 1/0288 601/40 |
| 2012/0136284 | A1* | 5/2012 | Land | A63B 21/00065 601/5 |

(Continued)

FOREIGN PATENT DOCUMENTS

| | | |
|---|---|---|
| CN | 102941579 A | 2/2013 |
| CN | 206393633 U | 8/2017 |

(Continued)

OTHER PUBLICATIONS

Resna14y80sdc "Exoarm" RESNA, RERC on AAC and NSF, Apr. 20, 2014.

*Primary Examiner* — Suba Ganesan
*Assistant Examiner* — Aren Patel
(74) *Attorney, Agent, or Firm* — Richard C. Litman; Nath, Goldberg & Meyer

(57) ABSTRACT

The robotic gripping assist ("RGA") provides a user with additional grip strength by supporting and forcefully pushing a user's fingers and hand to a gripping position. Motors are supported on a user's forearm and act as a source for the forced movement. A flexible member is worn on the back of a user's hand. The motors individually draw in or let out wires that cause the flexible member to move from a gripping to non-gripping position, and may pivot the flexible member laterally to provide for ulnar and radial wrist flexion. By bending the flexible member downward, through reeling in wires below the member, the attached fingers of the user are forced into a gripping position. Lateral movement is provided by reeling in the wires on the side of the intended bending direction.

12 Claims, 32 Drawing Sheets

(56) References Cited

U.S. PATENT DOCUMENTS

| | | | |
|---|---|---|---|
| 2014/0336620 A1 | 11/2014 | Layman et al. | |
| 2015/0374575 A1* | 12/2015 | Kamper | A61H 1/0288 |
| | | | 601/40 |
| 2016/0332817 A1* | 11/2016 | Ahdoot | A41D 19/01582 |
| 2018/0125692 A1 | 5/2018 | Takenaka et al. | |
| 2018/0311570 A1* | 11/2018 | Buchanan | A63F 13/42 |
| 2019/0091091 A1* | 3/2019 | Park | A61F 5/013 |

FOREIGN PATENT DOCUMENTS

| | | |
|---|---|---|
| JP | 2016129916 A | 7/2016 |
| WO | 2017133131 A1 | 8/2017 |

\* cited by examiner

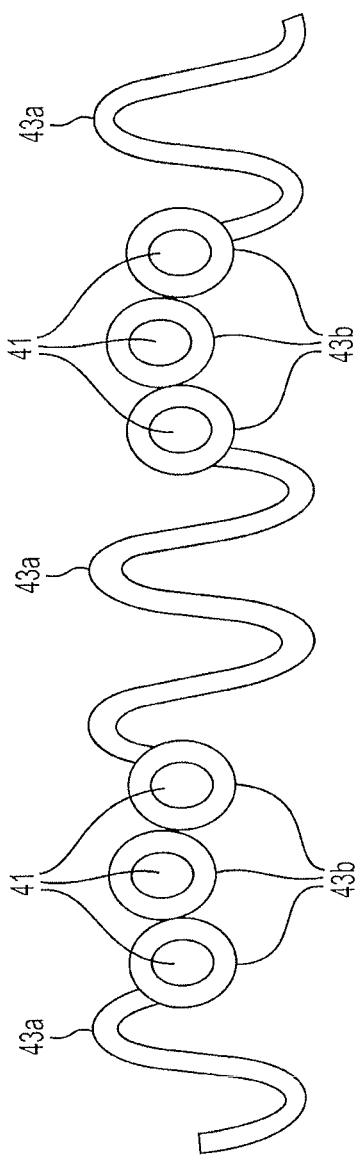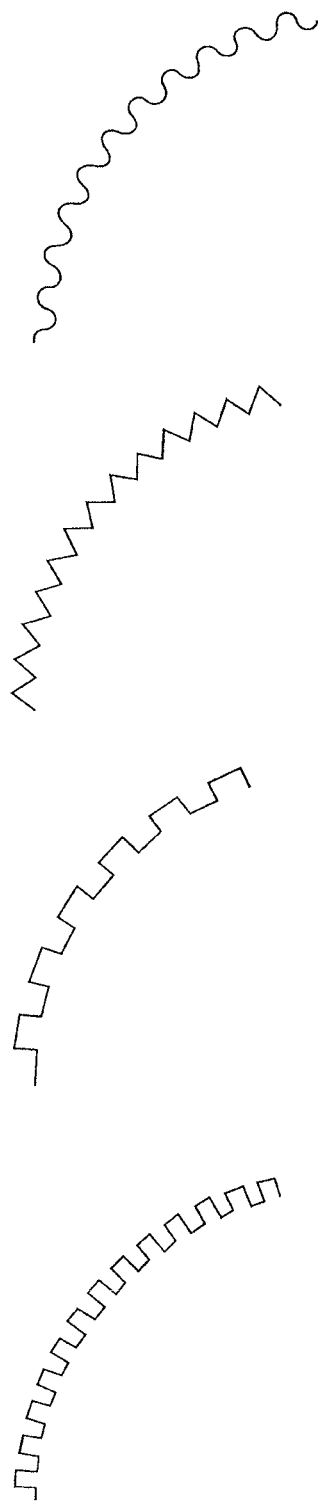

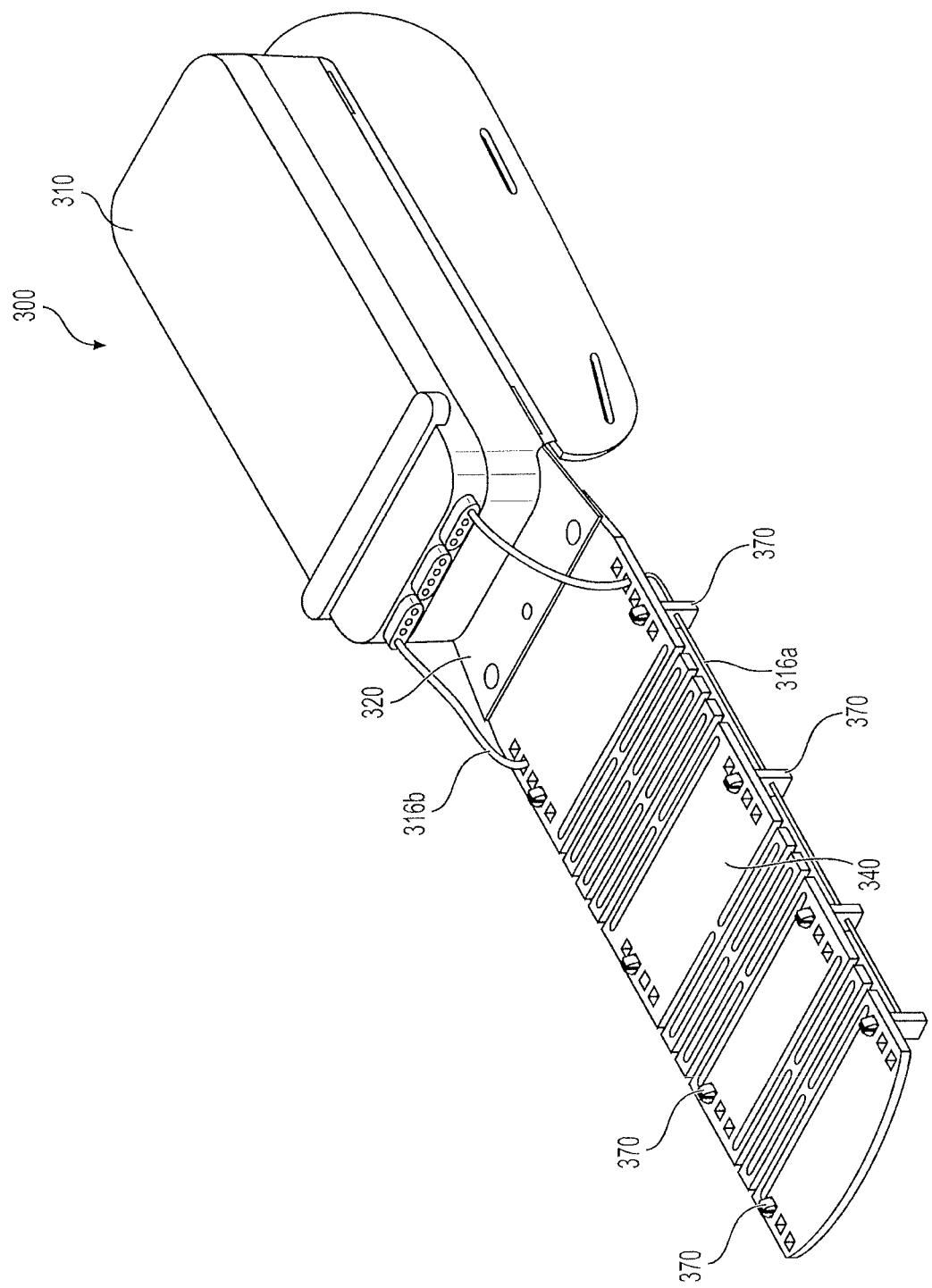

ROBOTIC GRIPPING ASSIST

CROSS-REFERENCE TO RELATED APPLICATION

This application is a continuation-in-part of U.S. patent application Ser. No. 16/351,458, filed Mar. 12, 2019.

BACKGROUND

Field

The disclosure of the present patent application relates to robotic human assistance, and particularly to a robotic gripping assist that may be worn on the lower arm and hand to provide additional grip strength for persons that have lost grip strength due to stroke and other neuromuscular impairments.

Description of the Related Art

Robotics includes several different research areas, procedures, and clinical and automatic programs, as well as those fields dealing with disability assistance. Applications of support robotics have focused on healing or improving physical afflictions, such as helping patients execute repeated healing actions. Robotic recovery apparatuses have the following advantages: high competence; restorative therapy; robot-supported exercises can be executed without assistance; precise outputs; and shortened recovery.

Research has shown that stroke patients who have been assisted by robots when executing repeated activities present a significant improvement in hand action performance. Furthermore, the use of robotics allows therapists to be relieved from time-consuming exercise tasks. Moreover, patients' rehabilitation situations can be easily evaluated using information recorded through the robotic exercise progress. Finally, wearable hand robotics can effectively enhance rehabilitation output after a stroke.

The hand is the primary part of the body that interacts with objects. Humans are capable of more precise hand actions than other creatures through a highly complex sensorimotor structure utilizing optical data and the physical hand mechanism (hand-eye coordination). People who have suffered a stroke display different disabilities and problems performing daily activities. New recovery procedures utilizing robot recovery devices are gaining the attention of researchers, programmers, and doctors. The primary aim of producing wearable hand robotics is to develop a device that facilitates patient recovery.

However, wearable robotic support arms have both hardware and software limitations. One major software obstacle occurs when the robot does not efficiently define and interact with the activities and purposes of the wearer. For example, the robot must be fit for use at home so patients can execute treatments on their own. In addition, present robotic support arms do not provide for ulnar and radial wrist deviation.

Thus, a robotic gripping assist solving the aforementioned problems is desired.

SUMMARY

The robotic gripping assist ("RGA") provides a user with additional grip strength by supporting and forcefully pushing a user's fingers and hand to a gripping position. At least one motor, a controller, and a power source are supported on a user's forearm and act as a source for the forced movement. A flexible or bending member is worn on the back of a user's hand. The motor(s) individually draw in or let out wires that cause the flexible or bending member to move from a gripping to non-gripping position, as well as to bend and pivot the flexible member sideways or laterally to provide for ulnar and radial wrist flexion. By bending the flexible member downward, through reeling in wires below the member, the attached fingers of the user are forced into a gripping position. The fingers are moved to a non-gripping position by reeling in wires above the flexible member. Lateral movement is provided by reeling in the wires on the side of the intended bending direction.

The RGA is attached to the user's hand and arm using a mitten and arm wrap that are connected directly to the RGA. Straps that wrap around the mitten and arm wrap are also used for securement. Once the device is secured to the user, the user can function normally with the benefit of added grip strength.

These and other features of the present disclosure will become readily apparent upon further review of the following specification and drawings.

BRIEF DESCRIPTION OF THE DRAWINGS

FIG. 7 is a diagrammatic side view of the bending member.

FIGS. 8A, 8B, 8C, and 8D are diagrammatic side views of alternative configurations of the wave portions of the bending member.

FIG. 20B is a perspective view of the third embodiment of a robotic gripping assist using the third clip.

Similar reference characters denote corresponding features consistently throughout the attached drawings.

DETAILED DESCRIPTION OF THE PREFERRED EMBODIMENTS

The robotic gripping assist ("RGA") provides a user with additional grip strength by supporting and forcefully pushing a user's fingers and hand to a gripping position. A motor, controller, and power source are supported on a user's forearm and act as a source for the forced movement. A bending member is worn on the back of a user's hand. The motor draws in or lets out wires that cause the bending member to bend or straighten. By bending the bending member, through rotating the motor in a first direction, the attached fingers of the user are forced into a gripping position. The fingers may be moved to a non-gripping position by rotating the motor in the opposite direction.

Figure 1A:
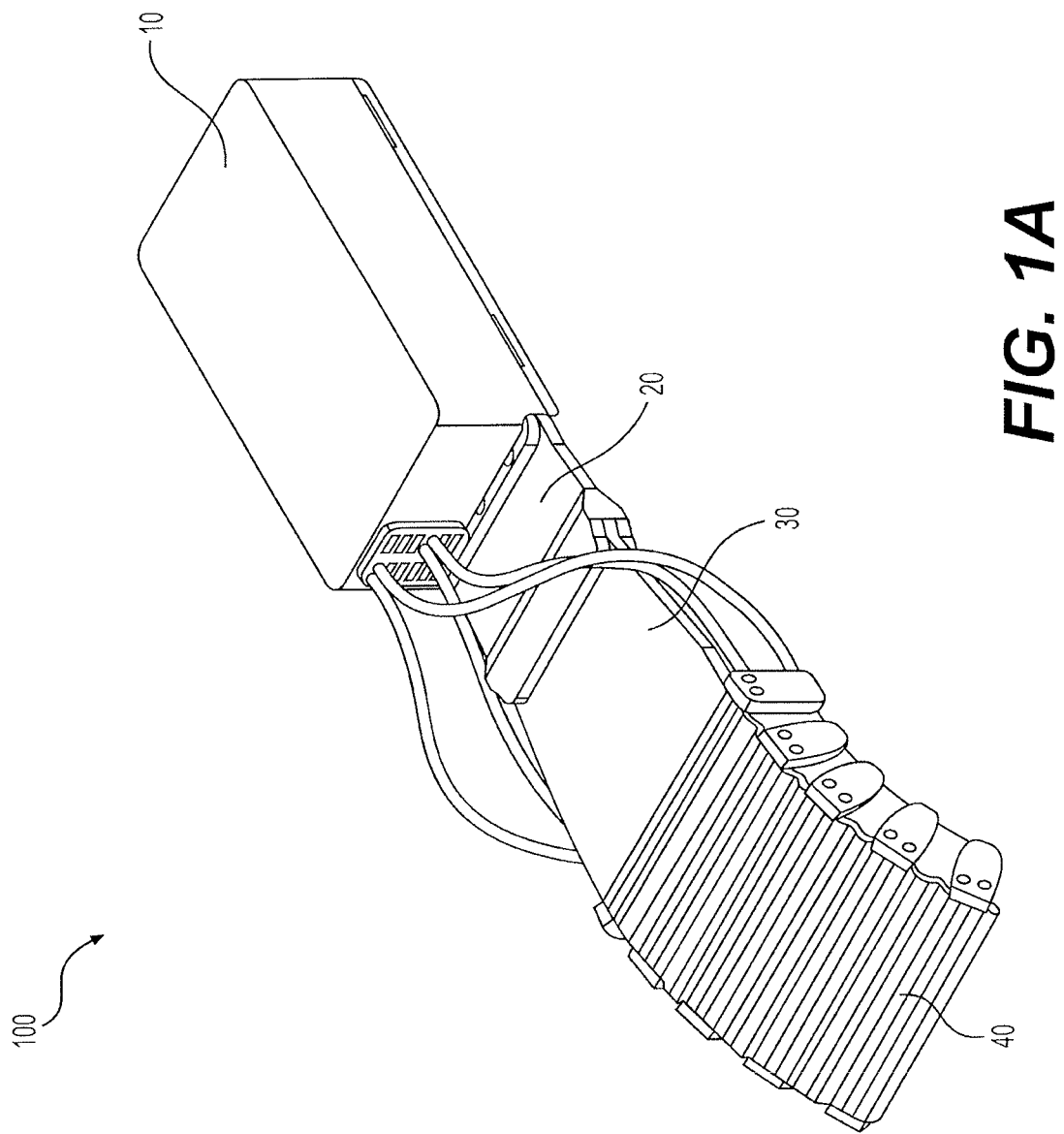
FIG. 1A is a perspective view of a first embodiment of a robotic gripping assist.
Figure 1B:
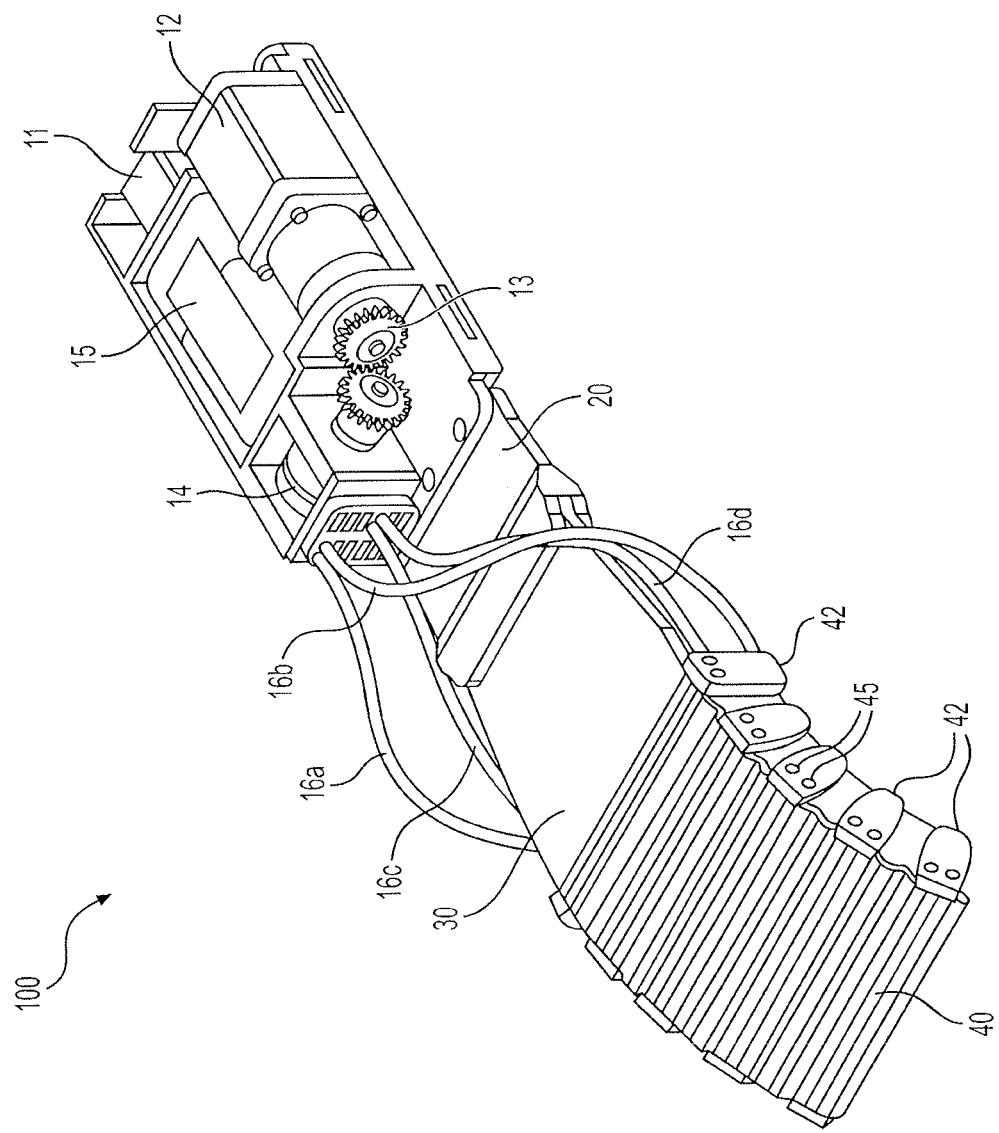
FIG. 1B is a perspective view of the robotic gripping assist of FIG. 1, shown with the protective cover removed from the arm box.

FIG. 1A shows a first embodiment of the RGA 100. The RGA 100 includes an arm box 10 connected to a base member 20, which is attached to a bending member 40 through an intermediate member 30. As seen in FIG. 1B, which shows the arm box 10 without its cover, the arm box 10 houses a power switch 11, a motor 12, a gear train 13, a spool 14, and a battery 15. Four wires 16a, 16b, 16c, and 16d are strung through support elements 42 attached to the sides of the bending member 40 along its length.

Figure 2:
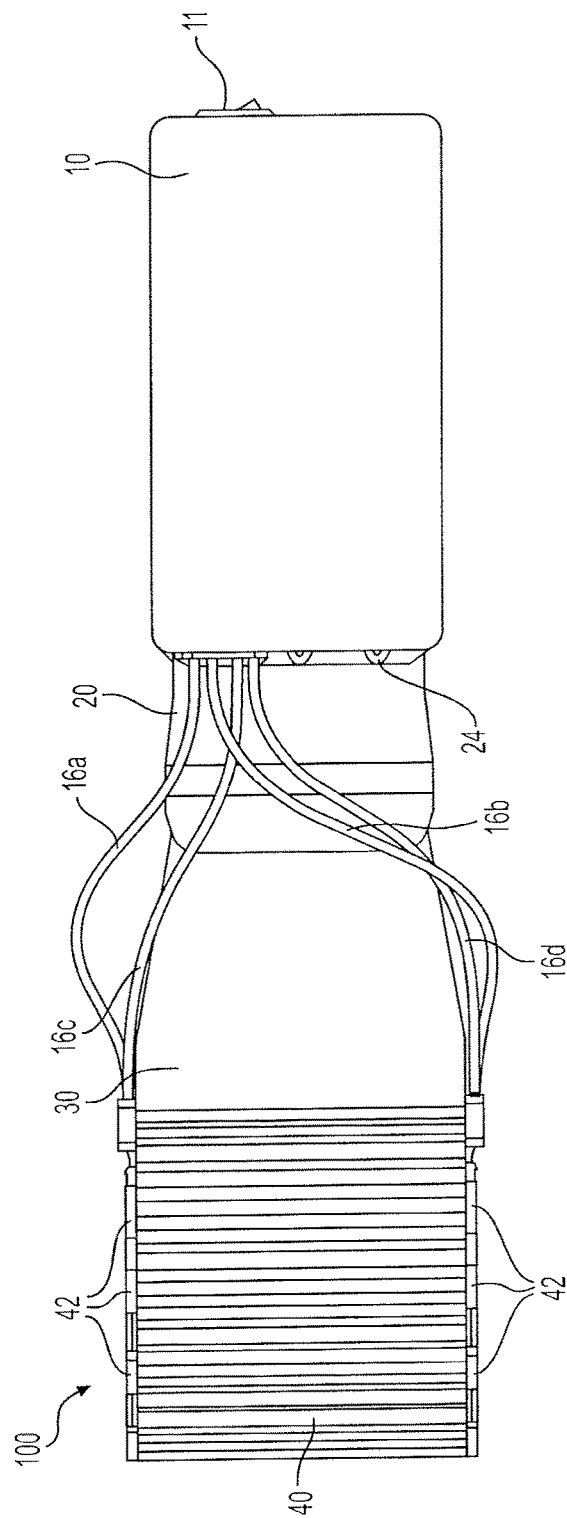
FIG. 2 is a top view of the robotic gripping assist of FIG. 1.
Figure 3:
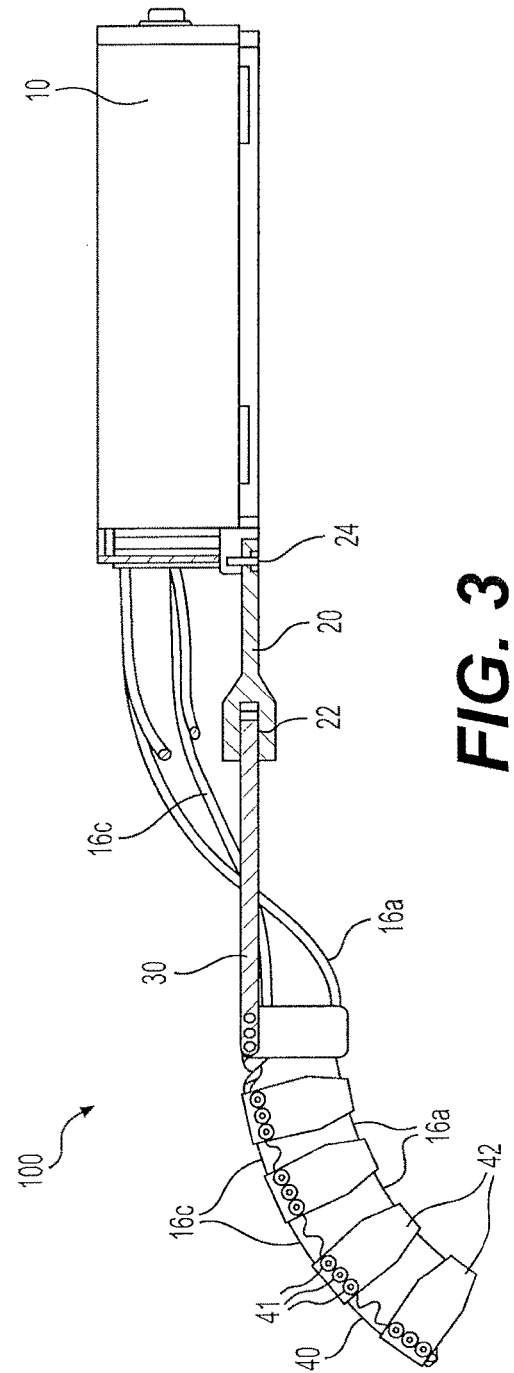
FIG. 3 is a side view of the robotic gripping assist of FIG. 1, shown with some components of the bending member in section.

FIGS. 2 and 3 are top and side views, respectively, of the RGA 100. FIG. 2 shows the bending member 40 is a corrugated, flexible belt having a rectangular shape (i.e., substantially uniform width) with support members 42 attached to opposing sides. As seen in FIG. 3, the tops of the support members 42 are connected to the bending member 40 and may be evenly spaced along its length. Two of the wires 16a, 16b are strung through the bottom of the support elements 42, one on each side of the bending member 40, and the other two wires 16c, 16d are strung through the top of the support members 42, with one on each side of the bending member 40. Since the tops of the support elements 42 are spaced apart, pulling on the bottom wires approximates only the bottoms of the support members 42. The approximation of the support member bottoms, while the tops of the support members 42 remain separated by the bending member 40 causes the bending member 40 to bend downward, as seen in FIG. 3. The bottoms of the support members 42 may be tapered inwards to allow for greater downward bend of the bending member 40 due to a greater range of approximation. While the lower wires 16a, 16b are pulled in, the upper wires 16c, 16d are let out to allow the bending member 40, which is located at the top of the support member 42, to bend downward. A proximal-most (proximal to the intermediate member 30) support member 42 may be connected to the intermediate member 30 to provide a first rigid support, towards which the other support members 42 will be pulled.

The base member 20 provides a rigid connection between the intermediate member 30 and the arm box 10. In the embodiment of FIGS. 1-3, the base member 20 has a planar proximal portion (proximal to the arm box 10), which is bolted to the arm box 10 by bolts 24, and a distal portion defining a channel 22. The channel 22 is dimensioned and configured to receive the proximal end of the intermediate member 30. The intermediate member 30 may be secured in the channel 22 by magnets to allow for quick assembly and disassembly. Since the forces of the intermediate member 30 acting on the base member 20 will primarily be rotational, the magnetic connection is adequate for securing the joint during operation. The intermediate member 20 may be dimensioned based on the user's hand size. Accordingly, a user with a large hand may use a device having a large intermediate member 20, and a user with a small hand may use a device with a small intermediate 20 member. In some embodiments, the intermediate member 20 may be interchangeable with intermediate members of different length so that the RGA 100 can accommodate users with different hand sizes.

Figure 4:
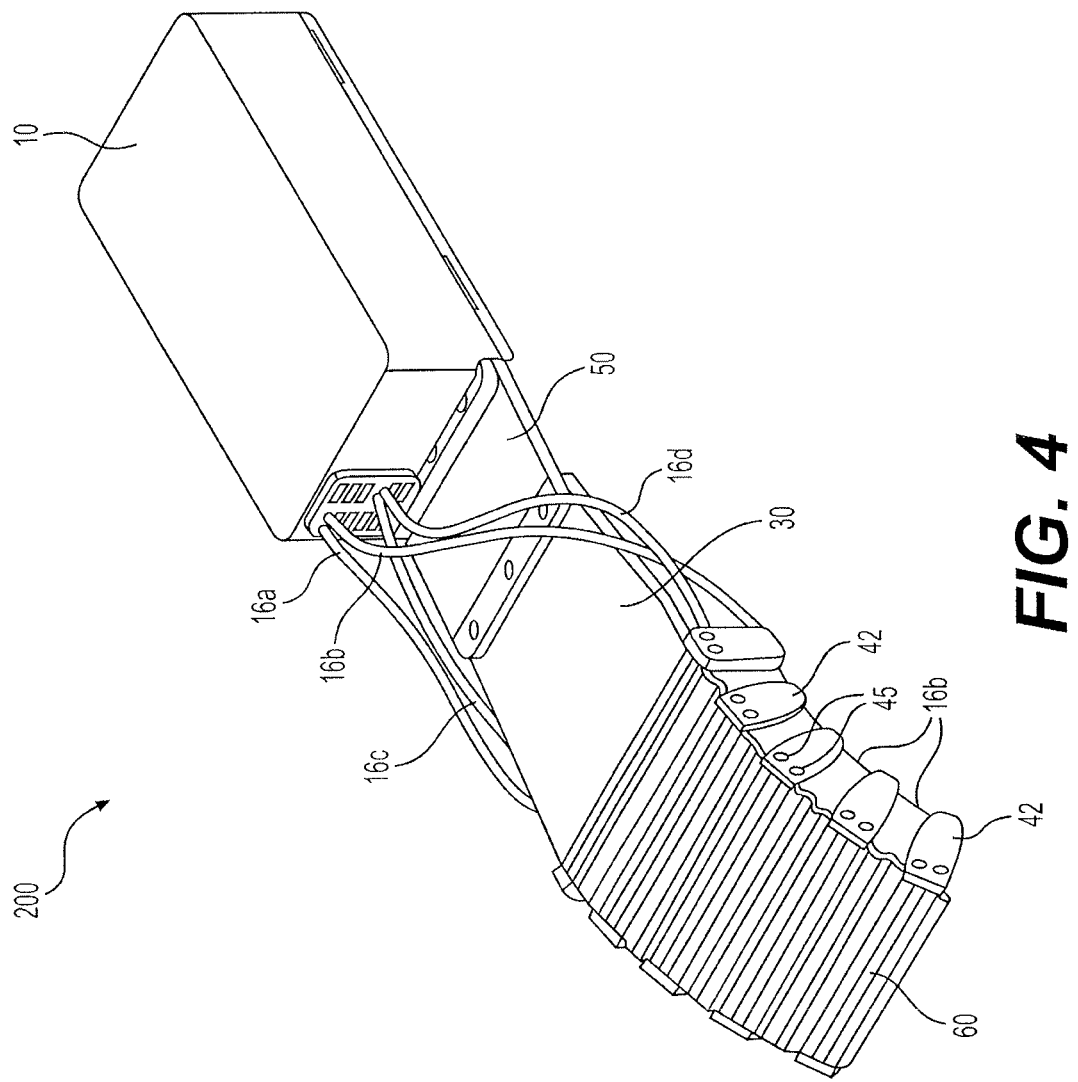
FIG. 4 is a perspective view of a second embodiment of the robotic gripping assist.
Figure 5:
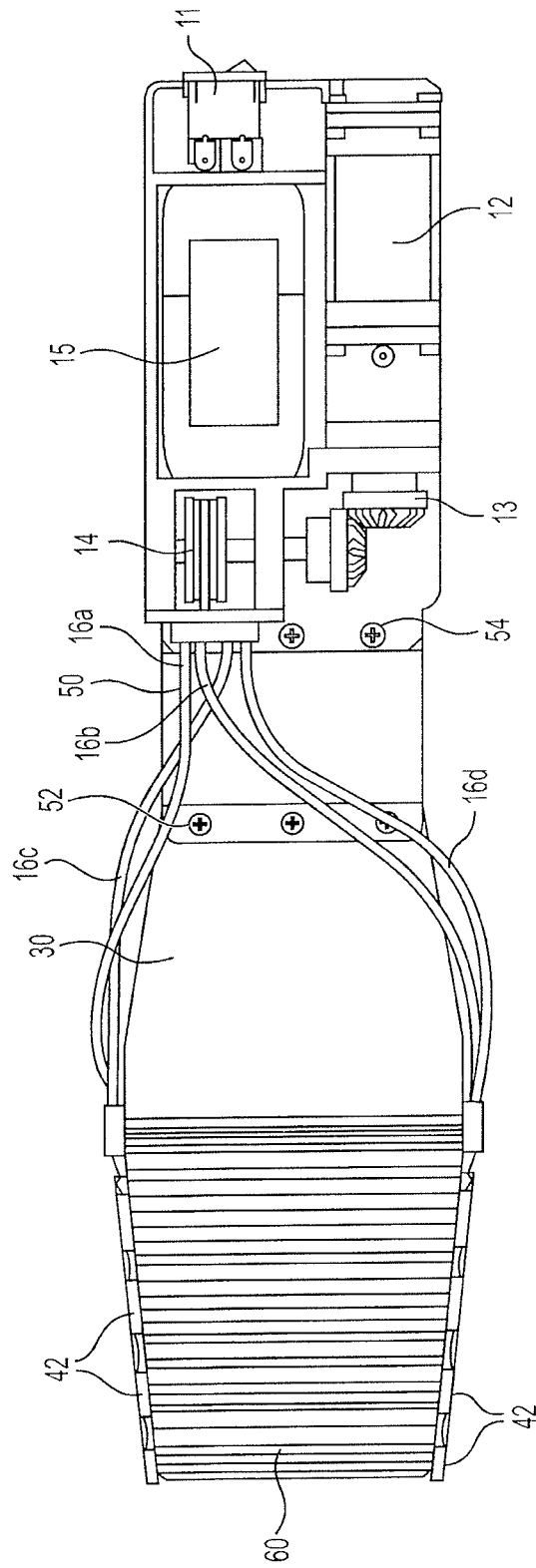
FIG. 5 is a top view of robotic gripping assist of FIG. 4, shown with the protective cover removed from the arm box.
Figure 6:
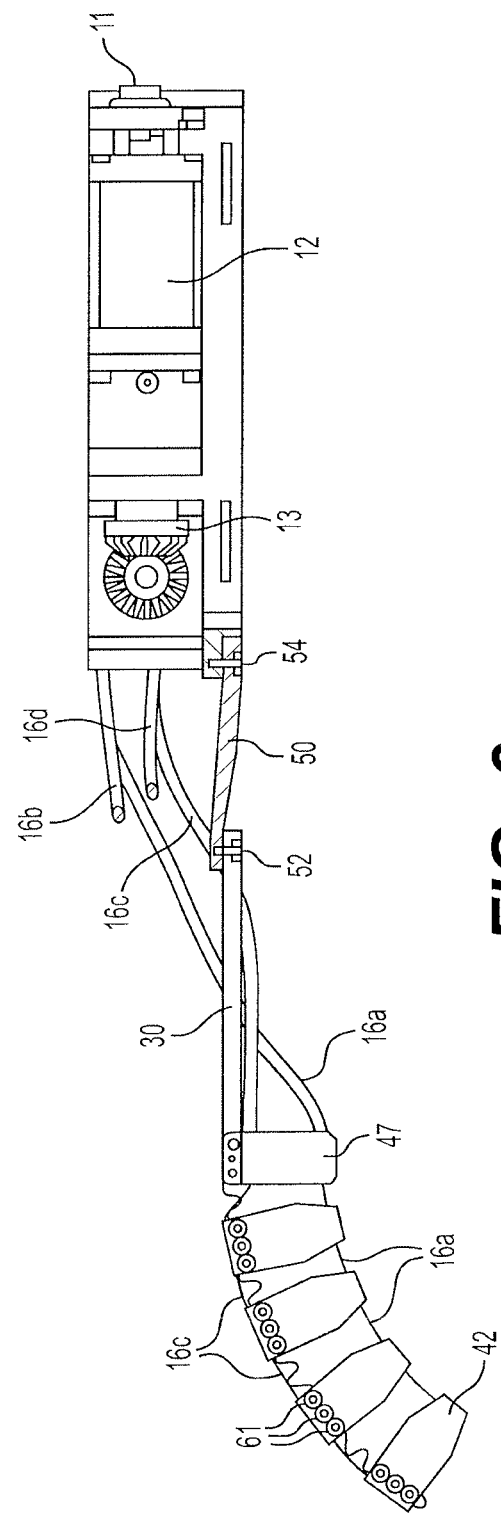
FIG. 6 is a side view of the robotic gripping assist of FIG. 4, shown with the protective cover removed from the arm box and with some components of the bending member in section.

A second embodiment of the RGA 200 is shown in FIGS. 4-6. The primary difference between the first and second embodiments is the shape of the bending member 60. The RGA 100 of FIGS. 1-3 has a rectangular shaped bending member 40 while the RGA 200 of FIGS. 4-6 has a bending member 60 that tapers in width inward towards its distal end. As best seen in FIG. 5, the bending member 60 tapers inwards towards its distal end to produce an end portion with a smaller width. This embodiment may be used for situations where there is not enough room to efficiently operate the embodiment having a full width end. The base member 50 is also different than the base member 20 of the first embodiment. In this embodiment, the base member 50 is similarly bolted to the bottom of the arm box 10, but does not have a channel 22 at the opposing end. Instead, the base member 50 bolts to the top of the intermediate member 30, as shown in FIG. 6. This embodiment may allow for more flexibility in the intermediate member/base member section of the device. Either base member 20, 50 may be used with either bending member 40, 60.

FIGS. 5 and 6 show the arm box 10 with the protective cover removed. A back of the housing of the arm box. 10 may hold a power switch 11 configured to be operated by a user. The switch 11 is connected to the motor 12, which may include an integrated motor controller. The output shaft of the motor 12 may be connected to a gear train 13 that changes the axis of rotation 90° to align the wire spool 14 with the bending member 60. As previously discussed, four wires 16a-16d are wrapped around the spool 14, with the two upper wires 16a, 16b wrapped in one direction and the two lower wires 16c, 16d wrapped in the opposite direction. Similar to the previous embodiment, the two upper wires 16a, 16b are strung through the top of the support members on opposing sides of the bending member 60 and the two lower wires 16c, 16d are strung through the bottoms of the support members 42 on opposing sides of the bending member 50. Since the wires 16a-16d are wrapped around the spool 14 in opposite directions, rotating the spool 14 will let the wires wrapped in one direction out and will simultaneously pull the wires wrapped in the other direction in. In some cases, the lower wires 16a, 16b will require more movement than the upper wires 16c, 16d. In these cases, the lower wires 16a, 16b can be wrapped around a larger spool and the upper wires 16c, 16d can be wrapped around a smaller spool.

FIG. 7 shows a diagrammatic side view of an embodiment of the bending member 40. The bending member 40 includes rigid rods or members 41 and a flexible belt 43a. The flexible belt 43a includes wave portions and sheath portions 43b encasing the rigid members alternately along its length. The wave portions extending between groups of sheathed rigid members 41 are shown as being two wavelengths, but may include more or less wavelengths to increase or decrease flexibility. The sheath portions 43b may include three cylindrical sheaths connected along their length with the middle sheath offset from the sheaths on opposing sides. The rigid rods 41 are located in the sheaths 43b for providing rigidity to the bending member 40 so that it primarily bends along its length dimension and not along its width dimension.

Figure 9A:
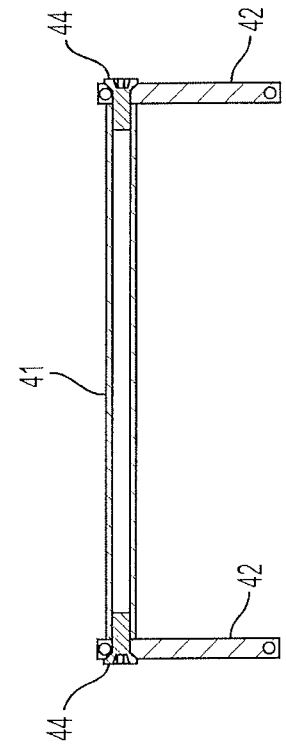
FIG. 9A is a diagrammatic side view of a support member attached to the bending member according to a first embodiment of an attachment mechanism.
Figure 9B:
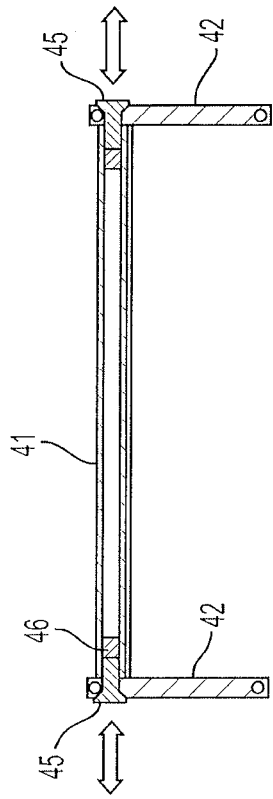
FIG. 9B is a side view in section taken through a rigid rod and opposing support members attached to the bending member according to the attachment method of FIG. 9A.
Figure 9C:
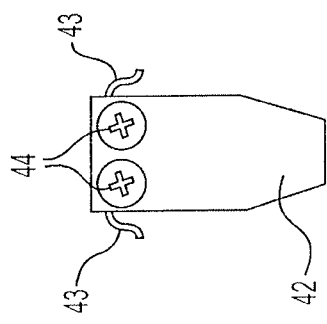
FIG. 9C is a diagrammatic side view of a support member attached to the bending member according to a second embodiment of an attachment mechanism.
Figure 9D:
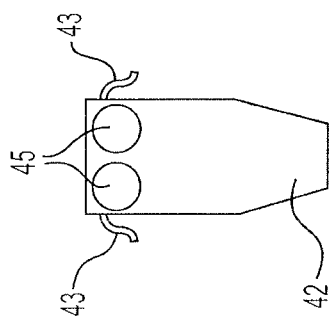
FIG. 9D is a side view in section taken through a rigid rod and opposing support members attached to the bending member according to the attachment method of FIG. 9C.

FIG. 3 also shows a side view of the bending member 40. As seen in FIG. 3, the rigid rods 41 provide rigid attachment points for the support members 42. Accordingly, the bending forces from the support members 42 are evenly distributed along the width of the bending member 40 by the rigid rods 41. By alternating the flexible wave portions of the belt 43a and the sheath portions 43b containing the rigid rods 41, the corrugated bending member 40 is provided with the necessary flexibility along its length for moving from a straight to a gripping position, while having the stability to prevent bending in a width direction and evenly distributing the forces from the support members 42. In addition to flexing downward when moving from a straight to a gripping position, the bending member 40 also experiences compression and extension along its length. The multiple wavelength wave portions between the sheath portions 43b allow the bending member 40 to compress and extend during operation. FIGS. 8A-8D show different shapes and relative dimensions that may be used for the wave portions of the bending member 40, e.g., square wave (FIGS. 8A, 8B), sawtooth (FIG. 8C), sine wave (FIG. 8D), etc. Different shapes and relative dimensions of the wave portions change the flexion, compression, and extension characteristics of the bending member 40. The aforementioned structure may be used on tapered bending member 60, such as in the second embodiment FIGS. 9A-9B show a first method for connecting the support elements 42 to the bending member 40. As previously discussed with regard to FIG. 7, the bending member 40 includes sections that contain three adjacent rigid rods 41. Each section of rods 41 may be connected to a support member 42 by two screws 44, one in each of the two outer rods 41. As seen in FIG. 9A-9B, two screws extend through holes in the upper portion of the support member 42 and into a threaded bore in the rods 41. FIGS. 9C-9D show a second method for connecting the support elements 42 to the bending member 40. In the second method, pins 45 are used in place of screws 44, and the pins 45 are held in place by a magnet 46 seated within the bore of the rods 41. This method may allow for quicker attachment and removal of the support member 42, since the pins 45 can be simply pilled out or pushed in. Alternatively, the pins 45 may be used for the proximal-most support member 42, and the screws may be used for the distal support members 42. This configuration will allow the bending member 40 to be easily removed from the intermediate member 30, while maintaining the security of screws 44 on the distal support members 42.

Figure 10B:
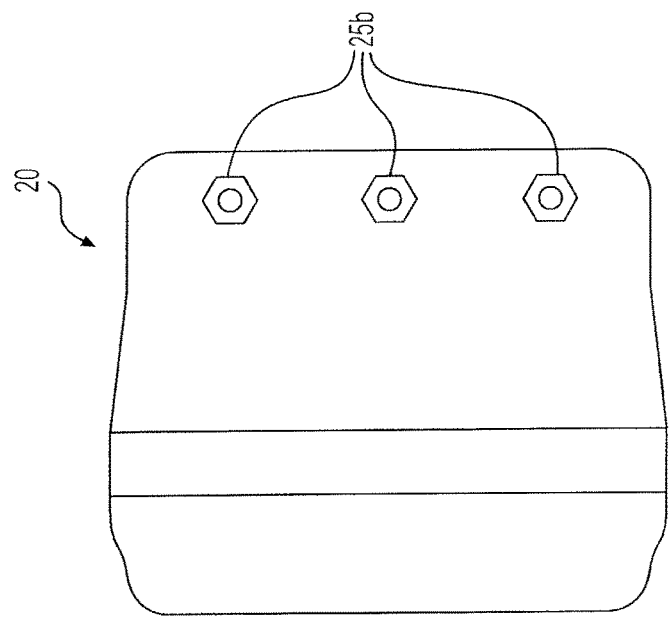
FIG. 10B is a bottom view of the base member of FIG. 10A.
Figure 10D:
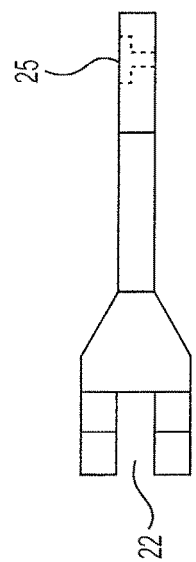
FIG. 10D is a side view of the base member of FIG. 10A.
Figure 10A:
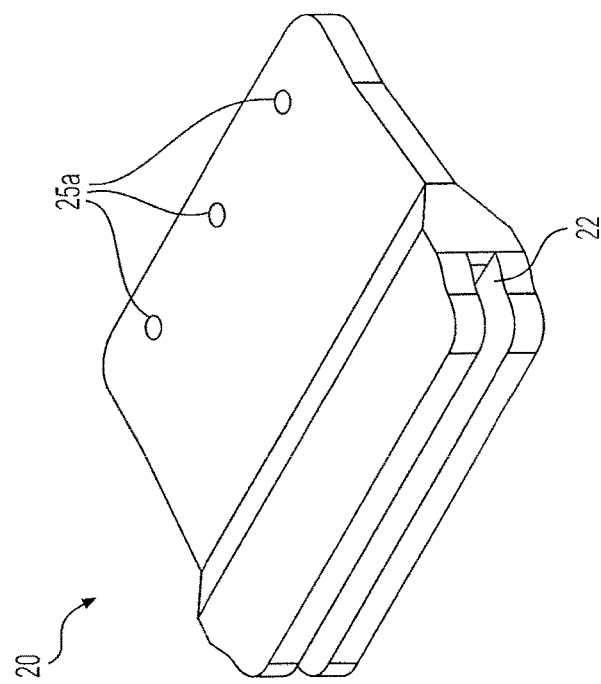
FIG. 10A is a perspective view of a first embodiment of the base member.
Figure 10C:
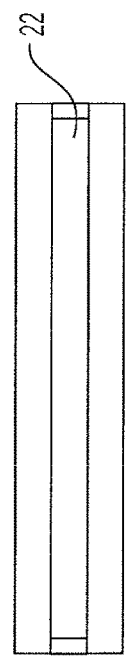
FIG. 10C is a front view of the base member of FIG. 10A.

FIGS. 10A-10D show details of the base 20 of FIGS. 1-3, which may use magnetic force to maintain a connection with the intermediate member 30. Similar to the previously mentioned magnetic pins 45, the magnetic connection allows for quick assembly and disassembly. As seen in FIGS. 10A and 10B, the proximal end of the base member 20 is a planar plate having holes 25a along its proximal edge for bolting to the arm box 10. As seen in FIGS. 10B and 10D, the holes 25b may have a countersink 25 to accept the bolt head 24 for maintaining a flat arm contacting surface. The distal end of the base member 20 defines a channel 22 running along its length for accepting the proximal end of intermediate member 30 (see FIG. 3). Magnets may be dispersed throughout the channel 22 portion for securing the intermediate member 30 once it is in place. As previously discussed, the primary forces of the intermediate member 30 on the base member 20 will be rotational. Therefore the structure of the channel 22, not the magnets, will counteract these forces.

Figure 11A:
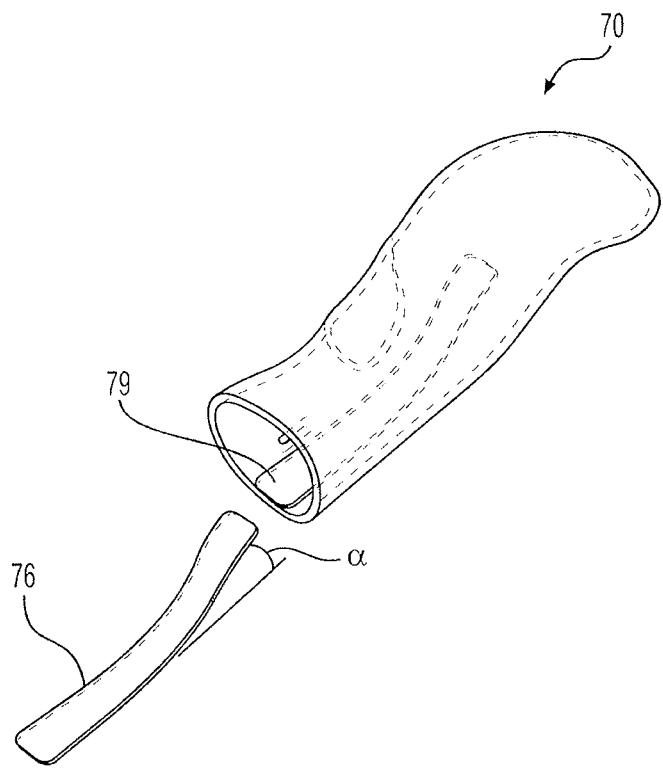
FIG. 11A is an exploded perspective view of a mitten and support plate for use with the robotic gripping assist.
Figure 11B:
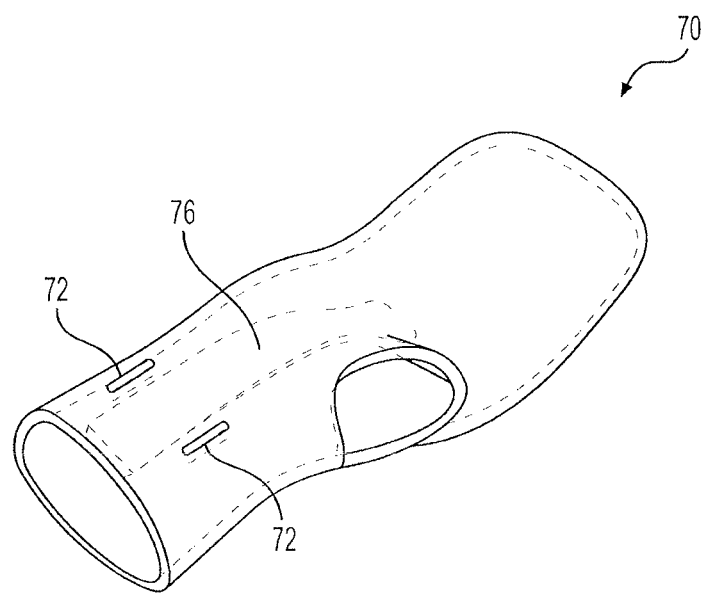
FIG. 11B is a perspective view of the mitten of FIG. 11A, shown with the support plate installed.
Figure 11C:
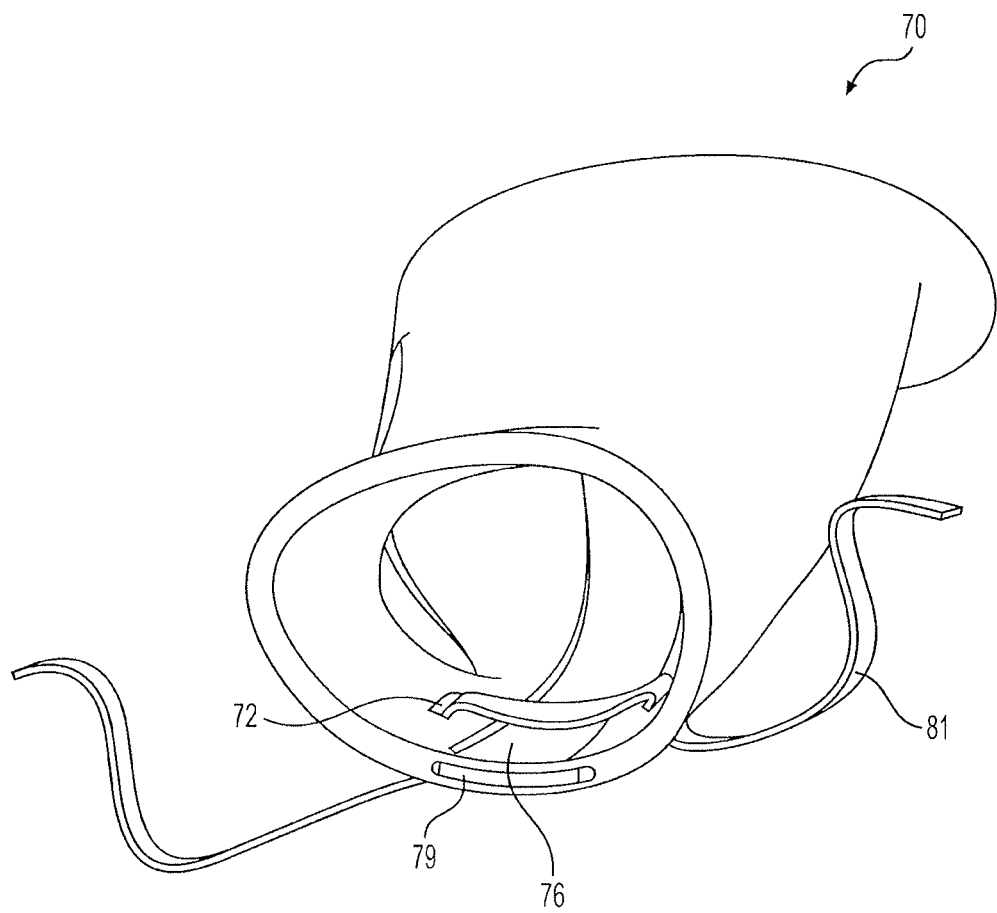
FIG. 11C is a rear perspective view of the mitten of FIG. 11A, shown with the support plate and connection strap installed.

FIGS. 11A-C show an exemplary mitten 70 that may be used with the RGA. The mitten 70 provides structure to the lower side of the user's hand and acts as an attachment medium for attaching the user's hand and arm to the RGA. The lower side of the mitten 70 includes a pocket 79 for receiving a support plate 76. The support plate 76 stabilizes the user's wrist and palm so that movements of the bending member 40 translate into curling the fingers, instead of pushing down the hand and wrist. As seen in FIG. 11A, the support plate 76 includes a substantially planar portion and an angled portion. The angled portion holds the user's wrist and palm in an upward position, and the planar portion stabilizes the support plate 76 against the user's forearm. With the palm and wrist locked in position, flexing and straightening the corrugated member 40 moves the fingers to a gripping and open position, respectively. The angle α of the angled portion may be adjusted for different hand positions to be better suited for different tasks. An increase in a will result in a raised palm, which may be more effective for griping objects in front of the user, while a decrease in a may result in a palm position better suited for overhead grabbing.

Figure 15:
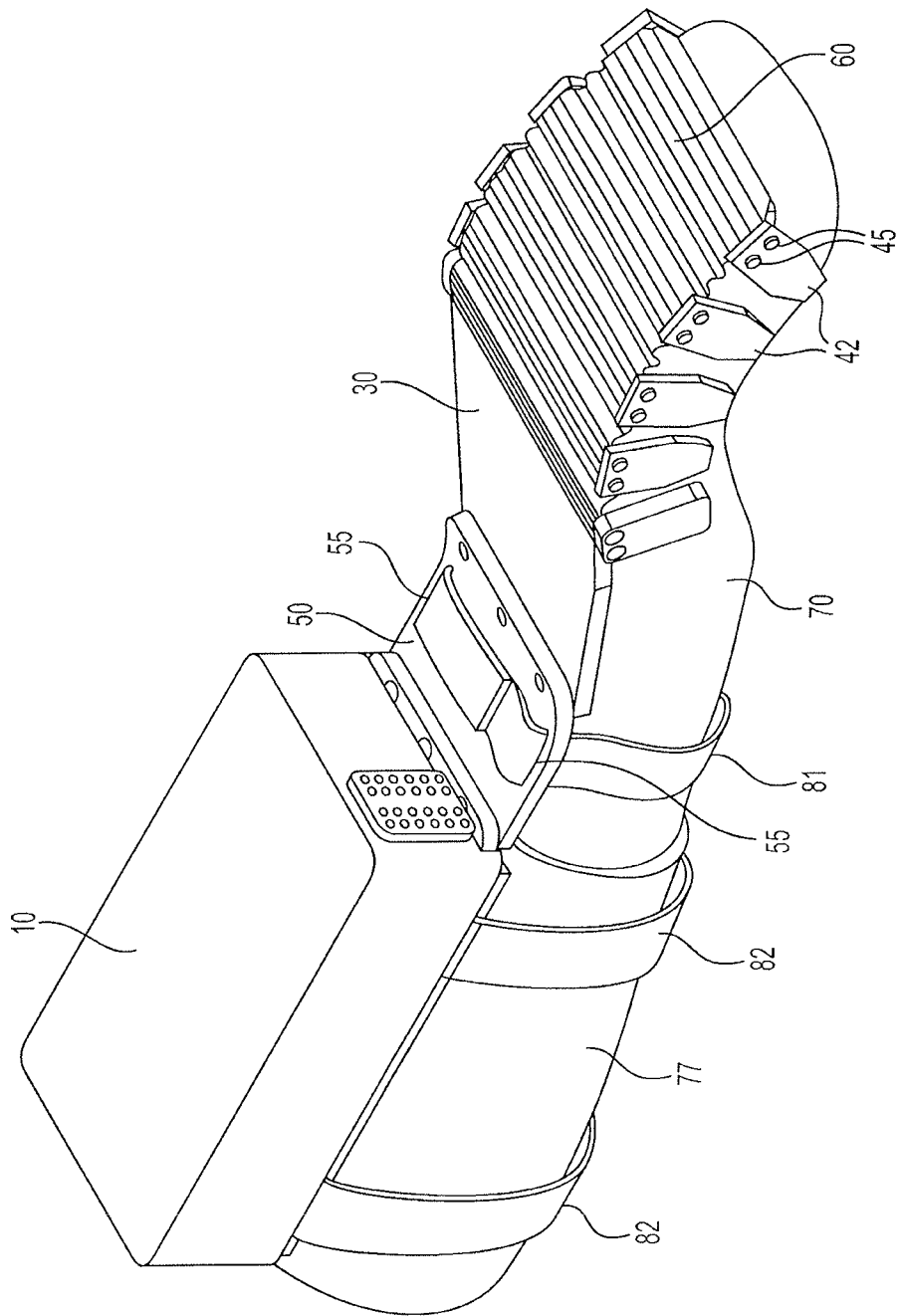
FIG. 15 is a perspective view of a robotic gripping assist, shown with the arm box and the bending member attached to the mitten and arm band, as it would be configured during use.

The mitten 70 also includes two slots 72 for receiving a connecting strap 81. When connecting the mitten 70 to the RGA, the connecting strap 81 sits above the support member 76 and extends out the two slots 72. The portion outside the slots 72 is wrapped upwards around the forearm to be threaded through slots 55 in the base member 50 for anchoring the ROS 200 to the user's arm, as seen in FIG. 15.

Figure 12A:
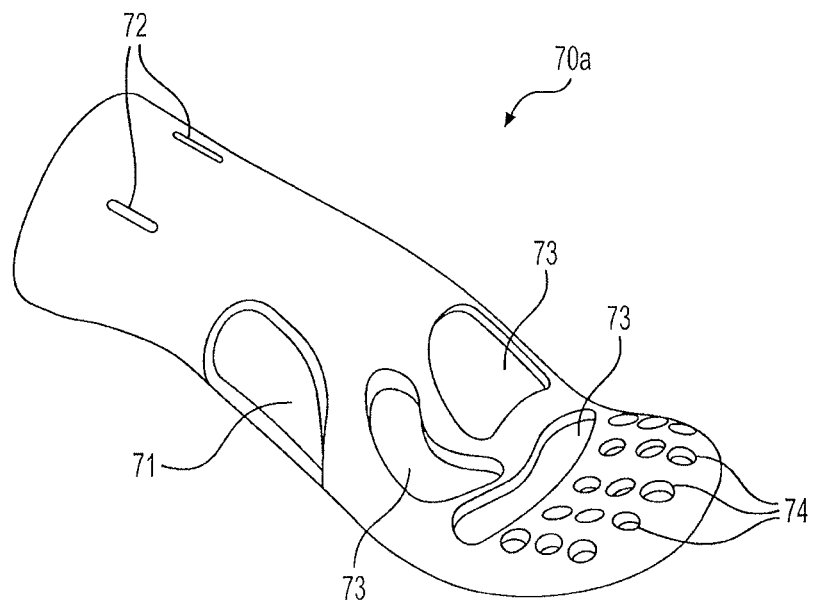
FIG. 12A is a perspective view of an embodiment of a mitten configured for providing sensory feedback.
Figure 12B:
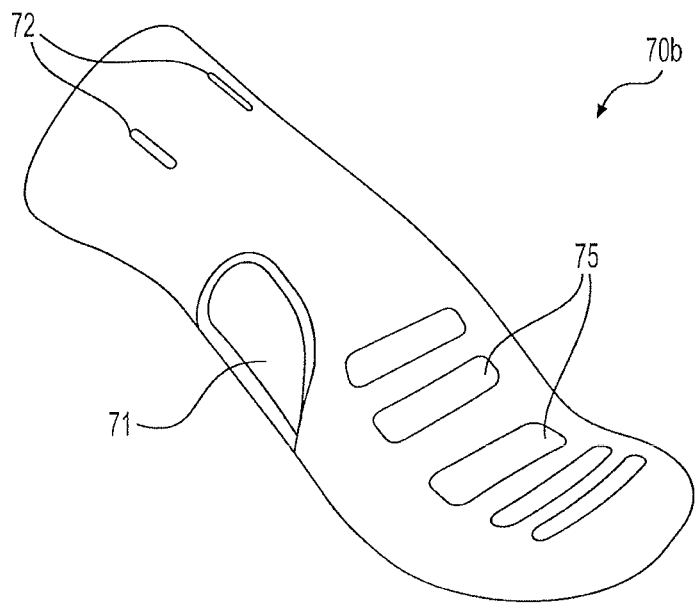
FIG. 12B is a perspective view of another embodiment of a mitten configured for providing additional grip.

FIGS. 12A-12B show two embodiments 70a, 70b of the mitten 70 that can be used with the RGA. The mitten 70a of FIG. 12A is designed for tasks that involve sensory feedback from the fingers/hand, as well as for tasks that benefit from the hand staying well ventilated. Accordingly, there are multiple openings 73, 74 in the palm and fingers of the mitten 70a. Specifically, there are multiple smaller holes 74 extending down the length of each finger, as well as multiple large holes 73 in the palm. These holes 73, 74 allow for direct contact between the user's skin and the object being touched, thus allowing the sensors in the user's hand to give accurate feedback. The mitten 70a also defines a large hole 71 in its side for the thumb to extend out from the glove or mitten 70a, since the RGA is not intended to power the thumb. FIG. 12B shows an embodiment of a mitten 70b that is used to enhance the user's grip. The gripping strips 75 may be made of high friction materials to provide better attachment to the object being gripped. The griping strips 75 may be connected to the mitten 70b by hook and loop fasteners to allow for replacement when worn out, or for substitution with gripping strips 75 having different characteristics, such as texture and material. Pressure sensing pads may be integrated into the gripping strip 75 to control movement of the RGA.

Figure 13A:
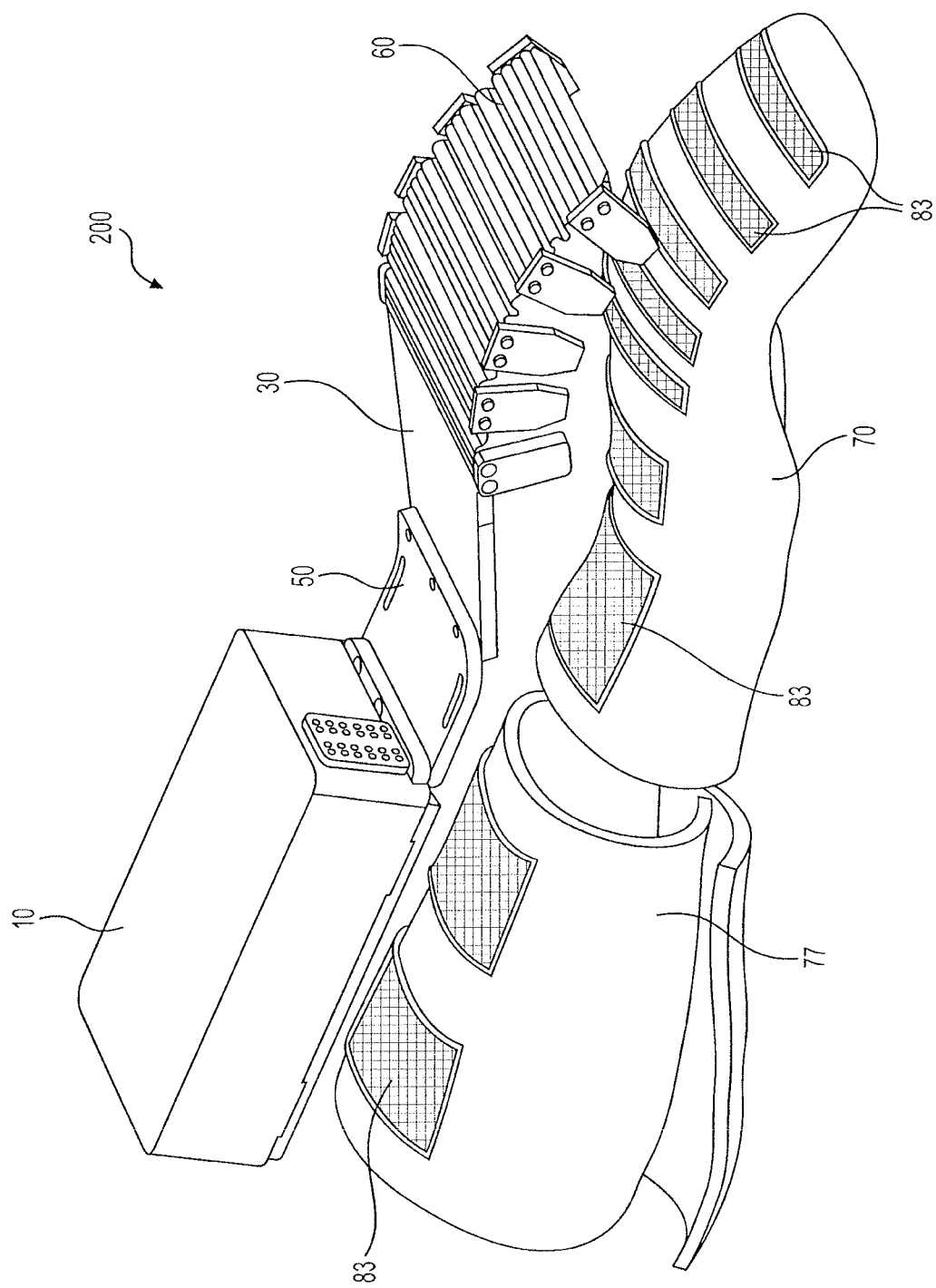
FIG. 13A is an exploded perspective view of the robotic gripping assist aligned with the mitten and arm band for attachment according to a first method of attachment to a user.
Figure 13B:
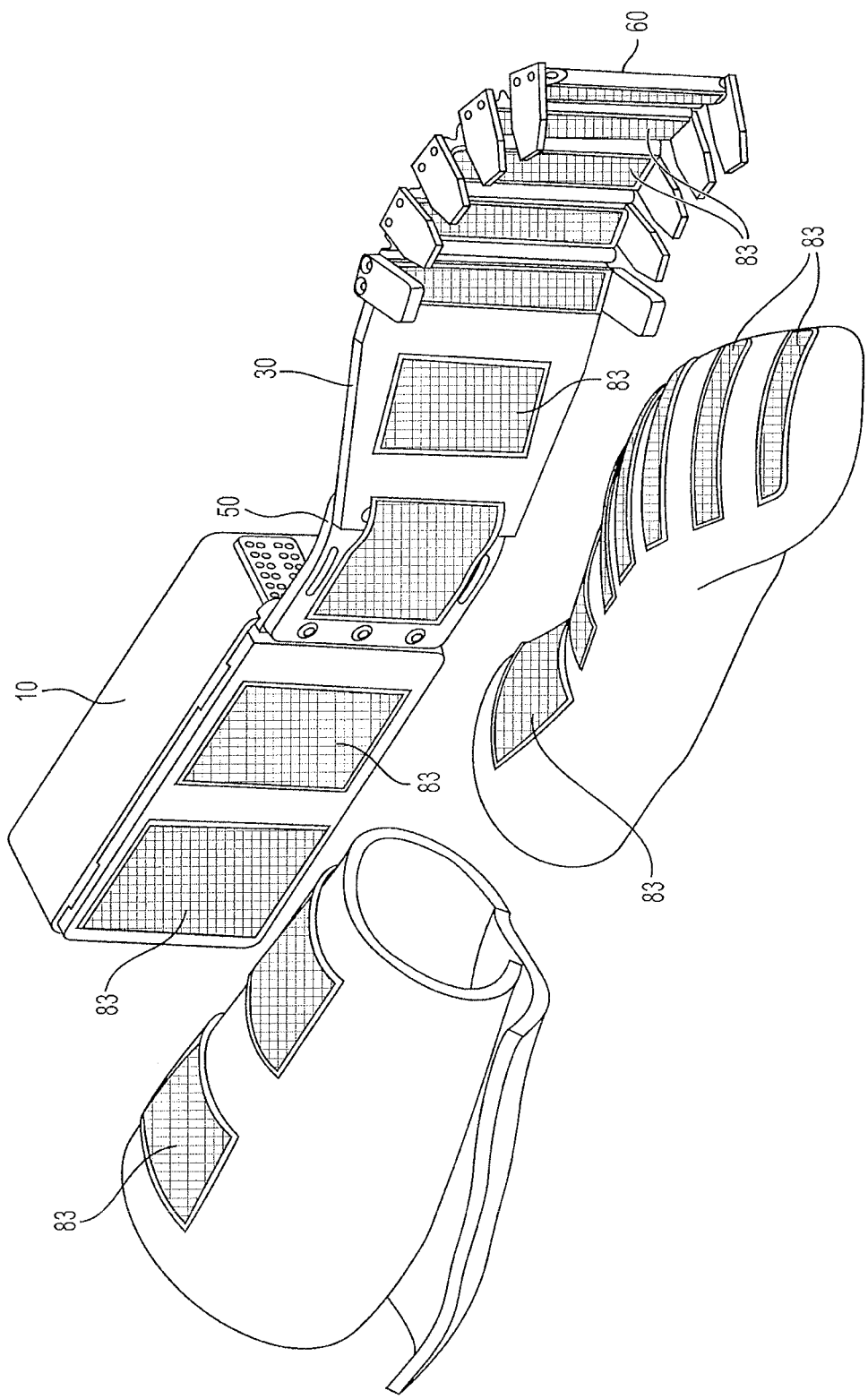
FIG. 13B is an exploded perspective view of the robotic gripping assist assembly of FIG. 13A, shown with the arm box and bending member lying on their side.

FIGS. 13A-13B show an embodiment of a mechanism for attaching the mitten 70 and an arm band or forearm sleeve 77 to the RGA 200 (wires have been removed from the RGA for clarity). The attachment mechanism includes two portions, the portion attached to the user and the portion attached to the RGA 200. In the embodiment shown in FIGS. 13A-13B, the attachment mechanism is patches of hook and loop fastening material 83. The mitten 70 and arm band 77 act as a support for attaching the hook and loop patches 83 to the user's arm. As seen in FIG. 13B, the hook and loop patches 83 on the mitten 70 have mating hook and loop patches 83 on the RGA 200. The hook and loop patches 83 on the bending member 60 are attached to the portion containing the rigid rods 41, since they will not deform during flexion. When the RGA 200 is aligned with the mitten 70 and the arm band 77, the hook and loop patches 83 will line up and create a secure connection between the user and the RGA 200.

Figure 14:
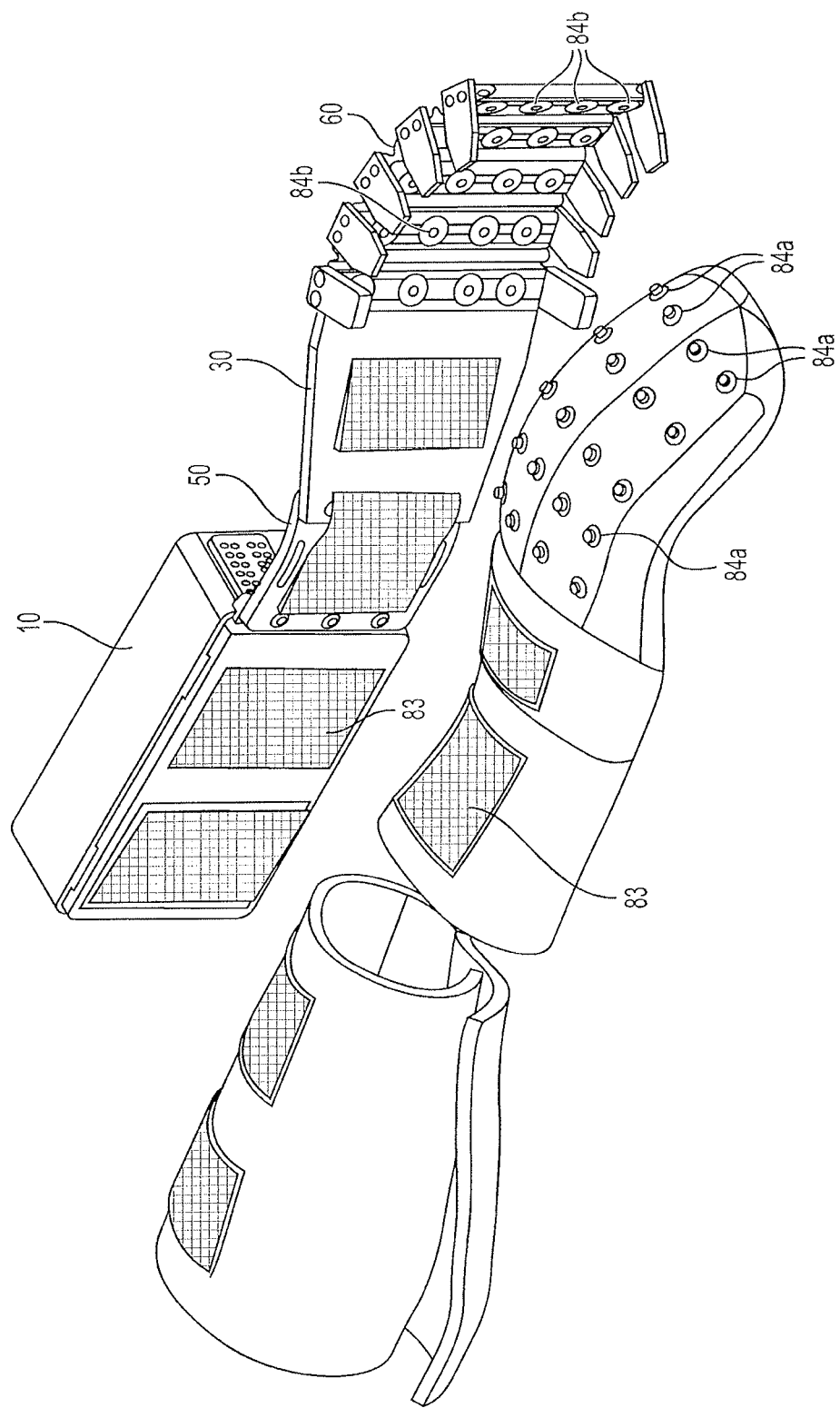
FIG. 14 is an exploded perspective view of a robotic gripping assist assembly similar to FIG. 13B but having a different method of securing the bending member to the mitten.

FIG. 14 shows an alternative embodiment of an attachment mechanism. The arm box 10, base member 50, and intermediate member 30 portions of this attachment mechanism are hook and loop patches 83, similar to the previous embodiment, and the bending member 60 is connected to the mitten 70 using snaps. As seen in FIG. 14, rows of male snaps 84a are attached to the hand portion of the mitten 70, and corresponding rows of female snap fasteners 84b are attached to the bending member 60 along the rigid rods 41. This embodiment may be used in scenarios where aligned securement between the hand and bending member 60 is critical.

FIG. 15 shows the RGA 200 fully connected to the mitten 70 and arm band 77 for use when attached to a user's arm. The top of the mitten 70 and arm band 77 are connected to the RGA using loop patches 83 and/or snap fasteners 84, as previously discussed, but cannot be seen in FIG. 15. The distal connected strap 81 extends up from the bottom of the mitten 70 and through holes in the base member 50. The two ends of the strap 81 are attached to create a tight loop around the mitten 70, the RGA 200, and the users arm within the mitten 70. The two proximal connection straps 82 each have arms that are attached at one end to the arm box 10. The arms connect to form loops for securing the arm box 10, which is the heaviest portion of the RGA 200, to the user's forearm, which is within the arm band 77.

The base member 20, intermediate member 30, and bending member 40 may each have their own stiffness characteristics that can be adjusted for user specific devices. The flexibility of the bending member 40, along with its ability to flex and extend the fingers, has already been discussed. However, the intermediate member 30 and base member 20 may also have flexibility to follow the profile of the user's hand and wrist. Typically, the bending member 40 will be the most flexible, in order to not hinder the gripping and straightening motions. The base member 20 will be the least flexible, to provide stability at the wrist, and the intermediate member will have an intermediate flexibility so that it can follow the user's hand when the wrist moves. In some cases, the individual flexibility of the bending member 40, intermediate member 30, and base member 20 may be determined based on the user's medical condition. The above flexibility pertains to all embodiments of the base member, intermediate member, and bending member.

Figure 16A:
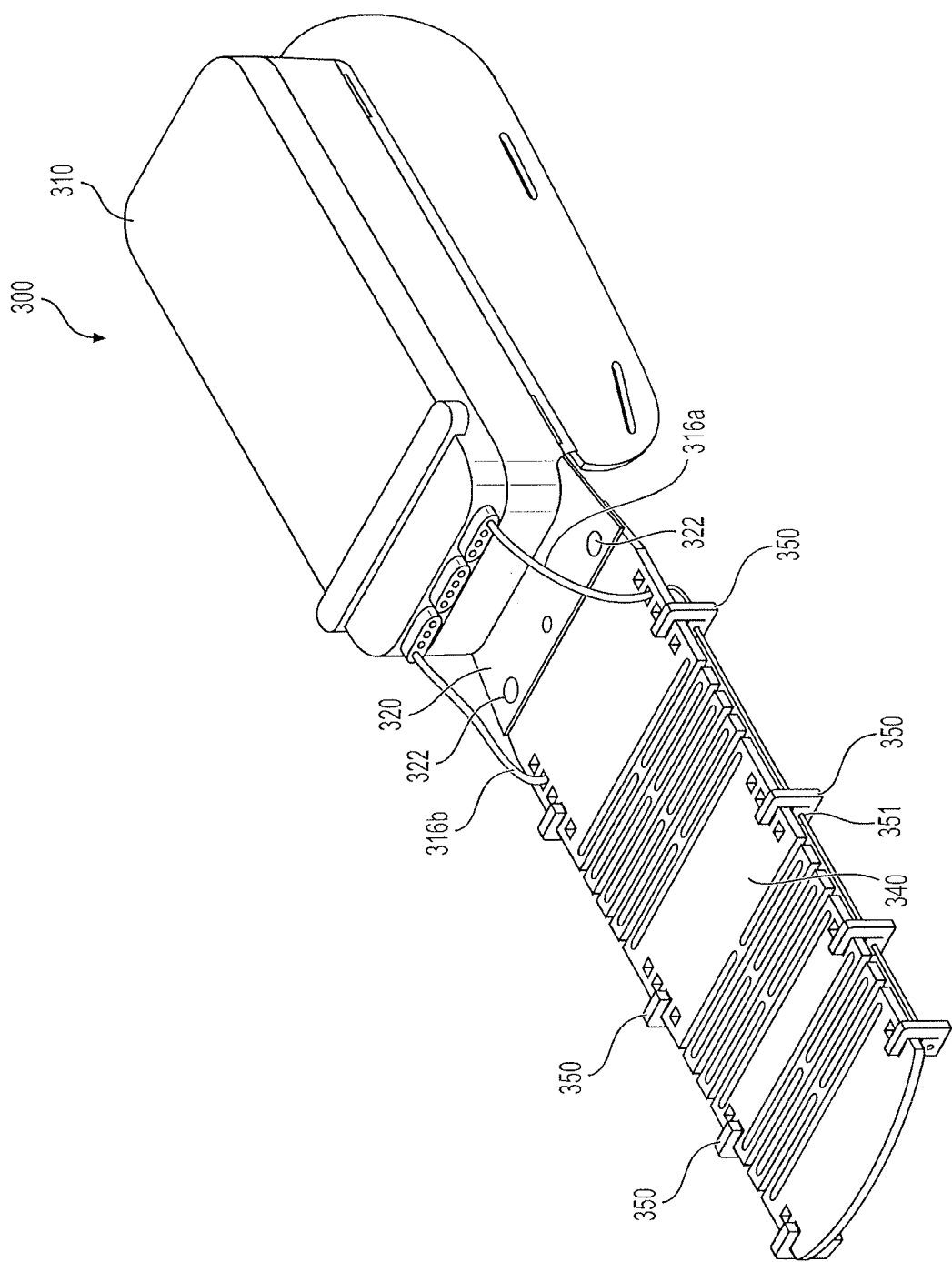
FIG. 16A is a perspective view of a third embodiment of a robotic gripping assist having only lower wires, shown in a non-gripping position.
Figure 16B:
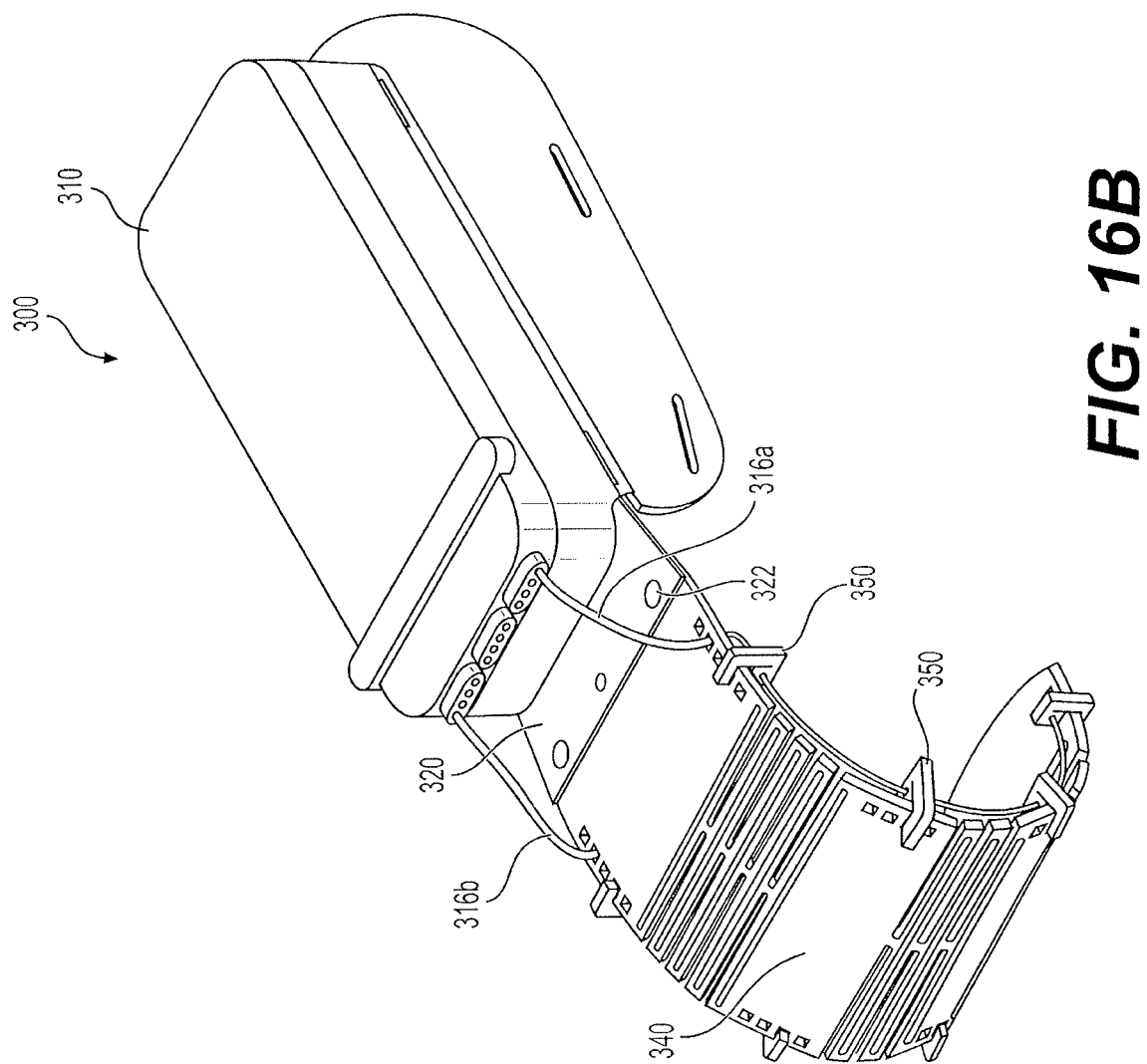
FIG. 16B is a perspective view of the robotic gripping assist of FIG. 16A, shown in a gripping position.
Figure 16C:
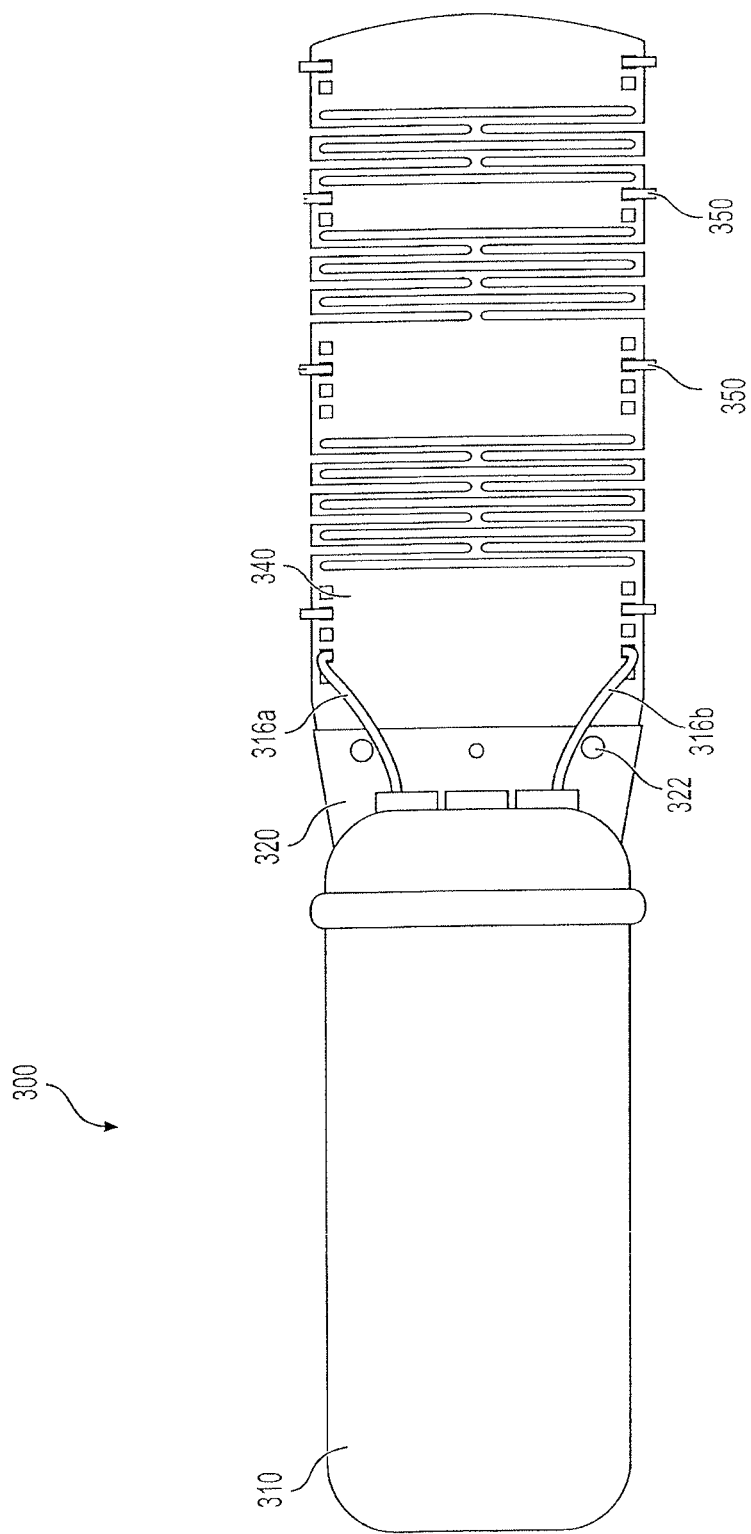
FIG. 16C is a top view of the robotic gripping assist of FIG. 16A.

A third embodiment of the RGA 300 is shown in FIGS. 16A-16C. The RGA 300 is similar to the previous embodiments, with the major differences being with respect to the previously discussed intermediate 30 and bending 40 members, and the support member 20 to which they are connected. In the present embodiment, a flexible member 340 may be formed out of a single piece of material, which serves the function of both the previously discussed intermediate 30 and bending 40 members. The flexible member 340 includes rigid portions 341a, 341c, 341e, 341g alternating with intervening flexible portions 341b, 341d, 341f spaced apart along its length (see FIG. 17). The flexibility of the flexible portions 341b, 341d, 341f may be provided by slots 342 defined in the flexible member 340. Other methods known in the art may be used to provide flexibility in the flexible portions 341b, 341d, 341f, such as an accordion shape. The flexibility of the flexible portions 341b, 341d, 341f may vary throughout each portion, as well as between each portion. Flexibility may be varied by changing the size and shape of the slots 342. The rigid portions 341a, 341c, 341e, 341g act as support surfaces for attaching the mitten 70, or a similar device wrapped around a hand of the user, while the flexible portions 341b, 341d, 341f are able to bend, allowing the flexible member 340 to move between the gripping and non-gripping positions shown in FIGS. 16A-16C. A mitten 70, or similar device wrapped around a hand of the user, may be attached to the flexible member 340 using any means discussed in this application. As seen in FIG. 16B, the rigid portions 341a, 341c, 341e, 341g remain substantially linear and the flexible portions arc downward when the flexible member is in a gripping position. In some embodiments, the rigid portions 341a, 341c, 341e, 341g may bend slightly when in a gripping position, but will remain closer to linear than the flexible portions 341b, 341d, 341f.

Figure 17:
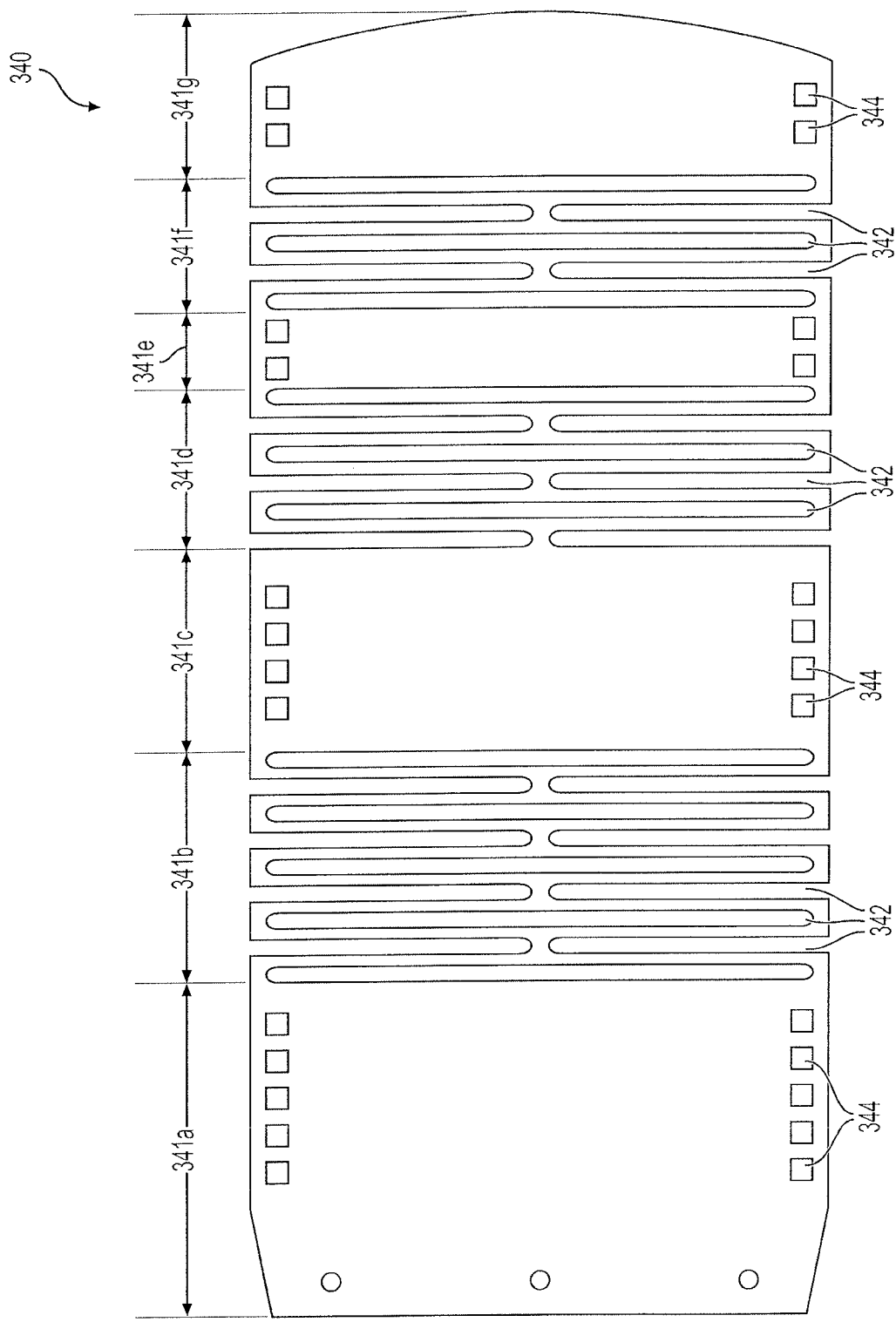
FIG. 17 is a top view of a flexible member for use with the third embodiment of a robotic gripping assist.

FIG. 17 shows an embodiment of the flexible member 340. In some embodiments, the rigid portions 341a, 341c, 341e, 341g may be designed to span the bones of a user's hand and the flexible portions 341b, 341d, 341f may be designed to span the joints of a user's hand. For example, a first rigid portion 341a may rigidly extend the flexible member over a user's metacarpal bone to the metacarpophalangeal joint (MCP). The first flexible portion 341b may be designed to rest above the user's MCP and provide the necessary flexibility to bend with the MCP. The second rigid portion 341c may rigidly extend across the proximal phalanx to the proximal interphalangeal joint (PIP). The second flexible portion 341d may be designed to extend over and flex with the user's PIP. The third rigid portion 341d may be designed to rigidly extend across the user's middle phalanx to the distal interphalangeal joint (DIP). The third flexible portion 341f may be designed to extend over and flex with the user's DIP. Finally, the fourth rigid portion 341g may be designed to extend over the user's distal phalanx. In some embodiments, the flexible member 340 may be designed for a specific user based on specific measurements of the user's hand. Furthermore, the rigidity of each rigid portion and flexibility of each flexible member 340 may be customized for a specific user based on the needs of the user. Multiple clip apertures 344 run along the length of the flexible member 340 for attaching clips that accept and retain the wires 316a-316d. FIG. 17 shows the clip apertures 344 as defining a square opening. However, it is within the scope of the present disclosure to have apertures of different shapes. There may be more clip apertures 344 than clips 350, which allows the placement of the clips to be customized based on a user's hand and finger size. Customizing the location of the clips may result in smoother movement and user comfort by distributing the forces to the right portions of the hand. The flexible member 340 may be manufactured by any method known in the art, such as additive manufacturing or laser cutting a solid sheet.

In the embodiment shown in FIGS. 16A-16C and 17, the flexible member 340 may be a substantially flat, elongated, belt-like member made of lightweight plastic or polymer material. The rigid portions 341a, 341c, 341e, 341g may be formed from continuous, uniform, non-slotted sheets of material. The flexible portions 341b, 341d, 341f may be formed from a plurality of rectangular sections having a central, elongated, enclosed slot defined therein, the rectangular sections being joined by central bridges defining left and right laterally extending open slots that are open at the opposing sides of the flexible member 340. When the flexible member 340 is flexed to the right, the open ends of the slots on the right side are compressed so that the rectangular sections may abut or approximate each other, while the open ends of the slots on the left side are spread apart, widening the gaps between the rectangular sections, as shown in FIG. 23C. The converse is true when the flexible member 340 is flexed to the left.

In addition to bending between gripping and non-gripping positions, the flexible member 340 is capable of flexing laterally for ulnar and radial deviation. Lateral flexion provides for the wrist of a user to move perpendicular to the gripping and non-gripping motion. Lateral wrist movement may be achieved by reeling the wire(s) 316a-316d on one side of the flexible member 340, while letting out the wire(s) 316a-316d on the other side (see FIG. 21 for an embodiment with four wires 316a-316d). For example, when flexing to the right, the wires 316b, 316d will be reeled in, thus pulling the right side of the flexible members 340 to the right by compressing the right side of flexible portions 341b, 341d, 341f, while the left wires 316a, 316c are let out to allow the left side of the flexible portions 341b, 341d, 341f to expand. FIG. 23C shows a flexible member 440 of a different embodiment flexing laterally, as discussed above.

The flexible member 340 may be connected to the base member 320 and arm box or housing 310 by three bolts 322, as seen in FIGS. 16A-16C. The wires 316a, 316b of the arm box 310 that manipulate the flexible member 340 into a gripping position may be connected to the flexible member 340 using multiple different clips 350, 360, 370, 380. The structure of the different clips 350, 360, 370, 380 may be designed to provide for different features. Some RGAs 300 may have only a single wire 316a, 316b below each side of the flexible member 340, and no wires 316c, 316d above the flexible member 340. By running the wires 316a, 316b below the flexible member, contracting the wires 316a, 316b will pull the flexible member 340 into a gripping position (shown in FIG. 16B). When tension is removed from the wires 316a, 316b, the natural rigidity of the flexible member 340 will spring the user's hand back to a non-gripping position. Other RGAs 300 may also include wires 316c, 316d extending above the flexible member 340, which can forcibly move the flexible member to a non-gripping position (see FIG. 21).

Figure 18:
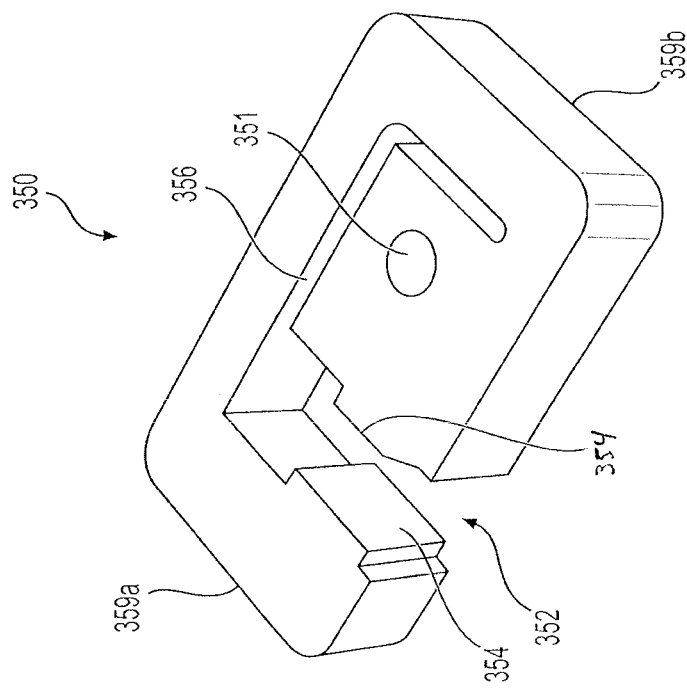
FIG. 18 is a perspective view of a first embodiment of a clip for attachment to the flexible member of a robotic gripping assist.

FIG. 18 shows a first embodiment of a clip 350 for attachment to the flexible member 340. The first clip 350 is designed for embodiments that run only a single wire 316a, 316b below each side of the flexible member 340, and does not provide for any wires 316c, 316d above the flexible member 340. The clip 350 has an upper portion 359a, which resides above the flexible member 340, and a lower portion 359b, which resides below the flexible member 340. A connecting port 352 is located between the upper 359a and lower 359b portions. The connecting port 352 defines upper and lower pegs 354 that snap into the clip apertures 344 of the flexible member 340. The clip 350 is attached to the flexible member 340 by sliding an edge of the flexible member 340 into the port 352 until the pegs 354 lock into one of the clip apertures 344 defined within the rigid portions 341a, 341c, 341e, 341g of the flexible members 340. The pegs 354 may be shaped to match the shape of the clip apertures 344. A slot 356 may extend down from an inner end of the port 352 to provide addition flexibility to the upper side of the port 352 for adding and removing the clip 350 from the flexible member 340. A wire guide 351 extends through the lower portion 359b of the clip 350 for accepting a wire 316a or 316b that extends out from the arm box 310. The wire guide 351 is an aperture extending through the clip 350 from the front to the back, which will be aligned with a length dimension of the flexible member 340 when attached. FIGS. 16A-16B show the clip 350 attached to the RGA 300 with the wires 316*a*, 316*b* running through the wire guides 351.

Figure 19:
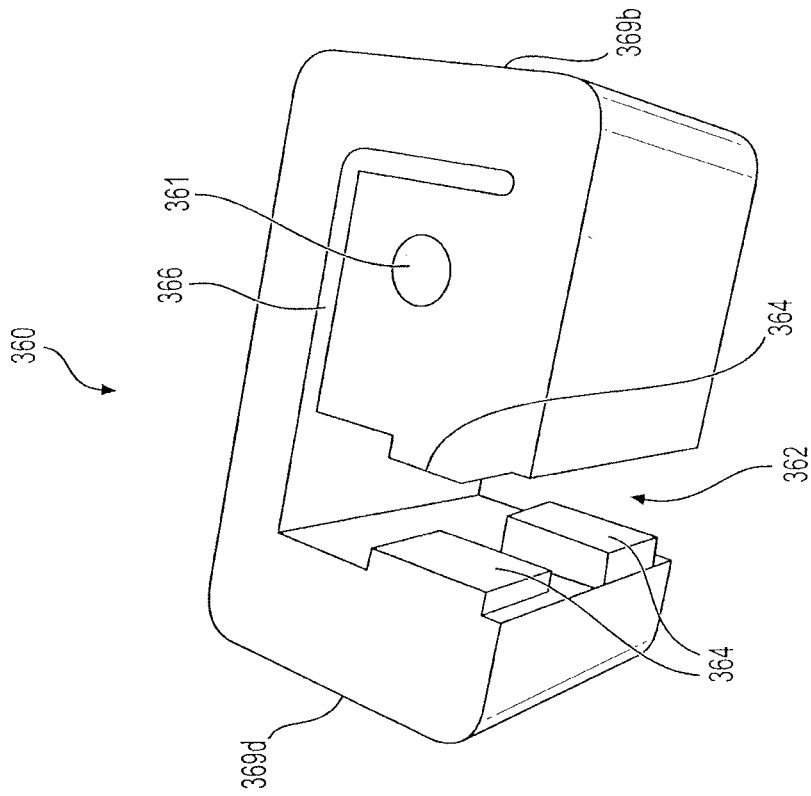
FIG. 19 is a perspective view of a second embodiment of a clip for attachment to the flexible member of a robotic gripping assist.

FIG. 19 shows a second embodiment of a clip 360. The second embodiment of the clip 360 is similar to the first embodiment of the clip 350, including upper portion 396*a*, lower portion 369*b* and flexing groove 366. However, the clip 360 includes two upper and two lower pegs 364 in the port 362. The clip 360 is secured to the flexible member 340 by snapping the pegs 364 into two adjacent clip apertures 344 on the flexible member 340.

Figure 20A:
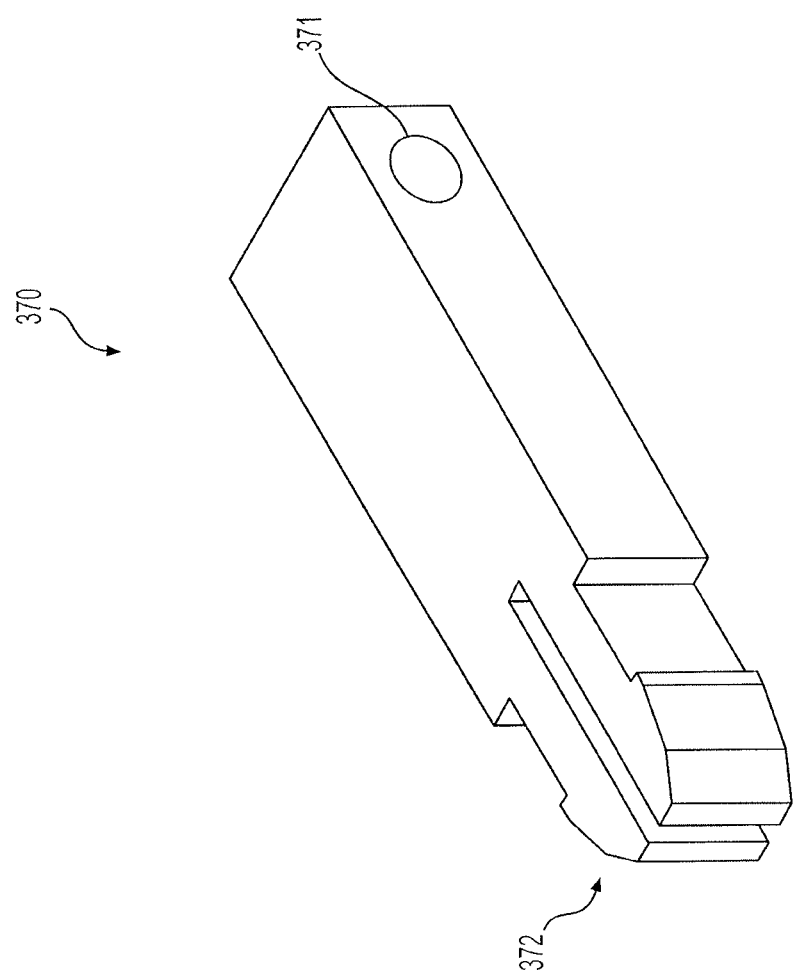
FIG. 20A is a perspective view of a third embodiment of a clip for attachment to the flexible member of a robotic gripping assist.

FIGS. 20A and 20B show a third embodiment of a clip 370. The clip is shaped as a post that snaps into a clip aperture 344 of the flexible member 340 from below. The top of the post defines a split snap-fit pin 372 that is designed to compress when being pushed through the clip aperture 344 and expand when fully inserted into the aperture 344 to lock the clip 370 in place. The lower portion of the clip 370 defines a wire guide 371 to accept and guide a wire 316*a*, 316*b* extending from the arm box 310. FIG. 20B shows the clip 370 locked into the flexible member 340.

Figure 21:
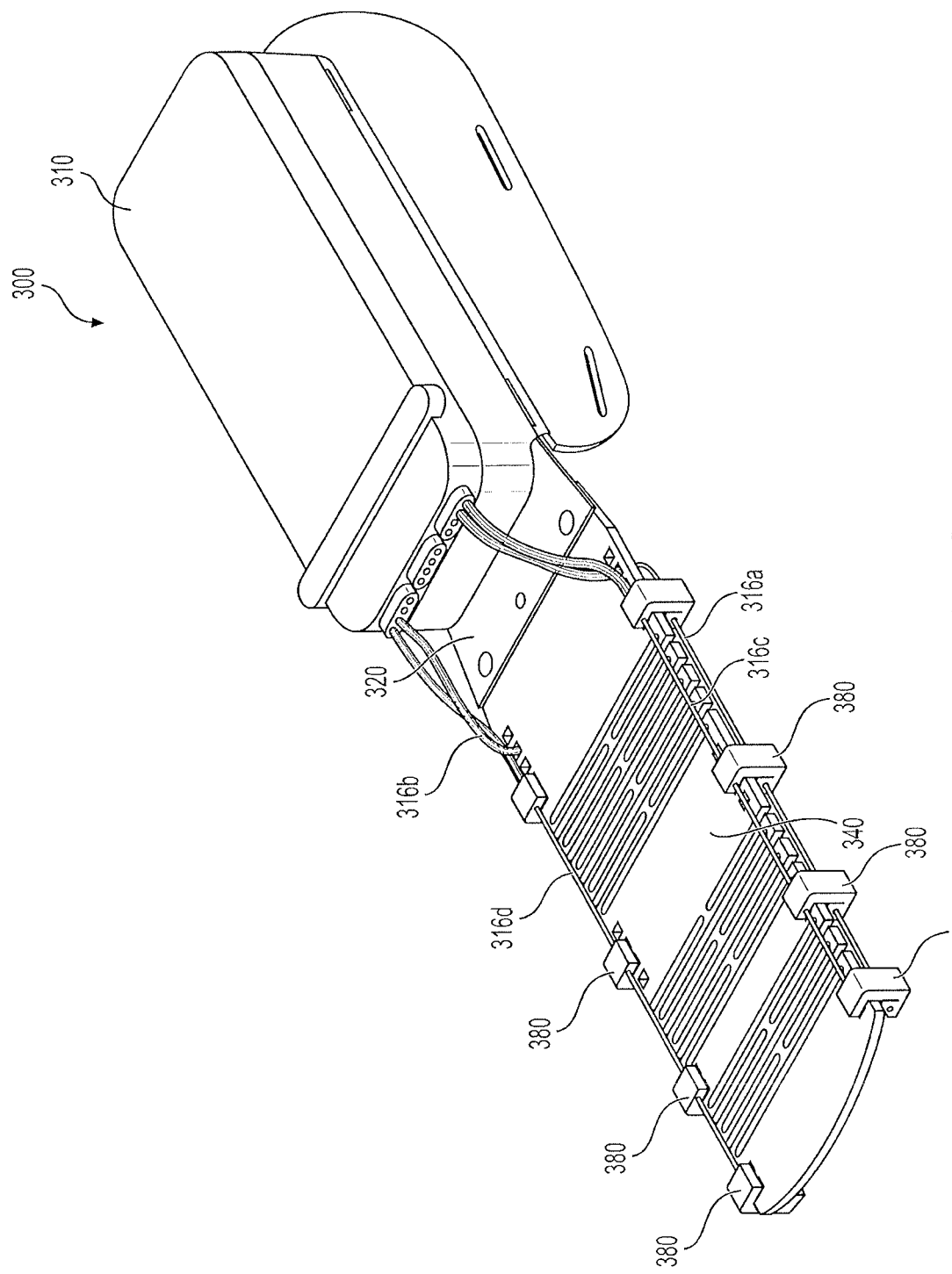
FIG. 21 is a perspective view of the third embodiment of a robotic gripping assist using a fourth clip, the robotic gripping assist including upper and lower wires.

FIG. 21 shows a perspective view of the RGA 300 with four wires 316*a*, 316*b*, 316*c*, 316*d*, two above and two below the flexible member 340. As previously discussed, the two wires 316*a*, 316*b* running above the flexible member 340 force the flexible member 340 from a gripping to a non-gripping position when contracted. Accordingly, when the RGA 300 is adjusting from a gripping to a non-gripping position, the upper wires 316*c*, 316*d* are reeled in and the lower wires 316*a*, 316*b* are let out.

Figure 22:
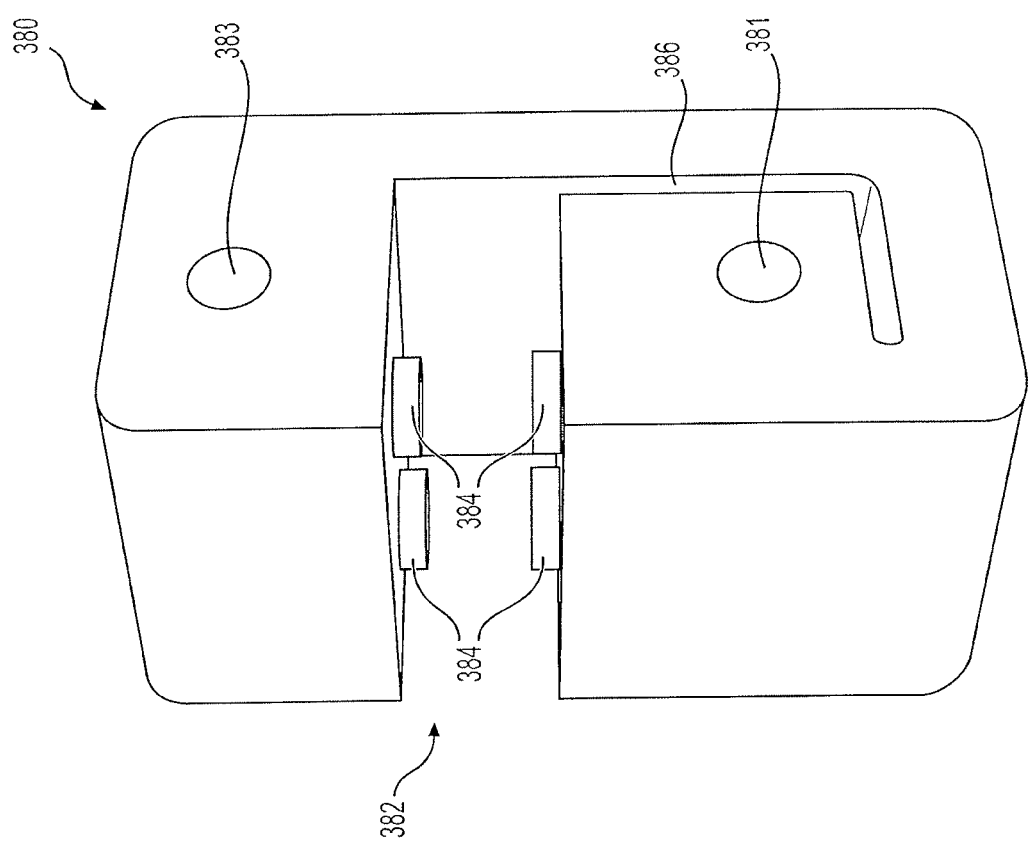
FIG. 22 is a perspective view of the fourth embodiment of a clip for attachment to a flexible member of a robotic gripping assist.

FIG. 22 shows a fourth embodiment of a clip 380 that may be used with an RGA 300 having two upper 316*a*, 316*b* and two lower wires 316*c*, 316*d*. The clip 380 is similar to the clip 360 of FIG. 19, since the clip 380 has two pegs 384 on the top and bottom of the port 382, and a flexibility channel 386. The clip 380 includes an upper wire guide 383 and a lower wire guide 381. Each wire guide 383, 381 is an aperture extending from the front to the back of the clip 380.

Figure 23A:
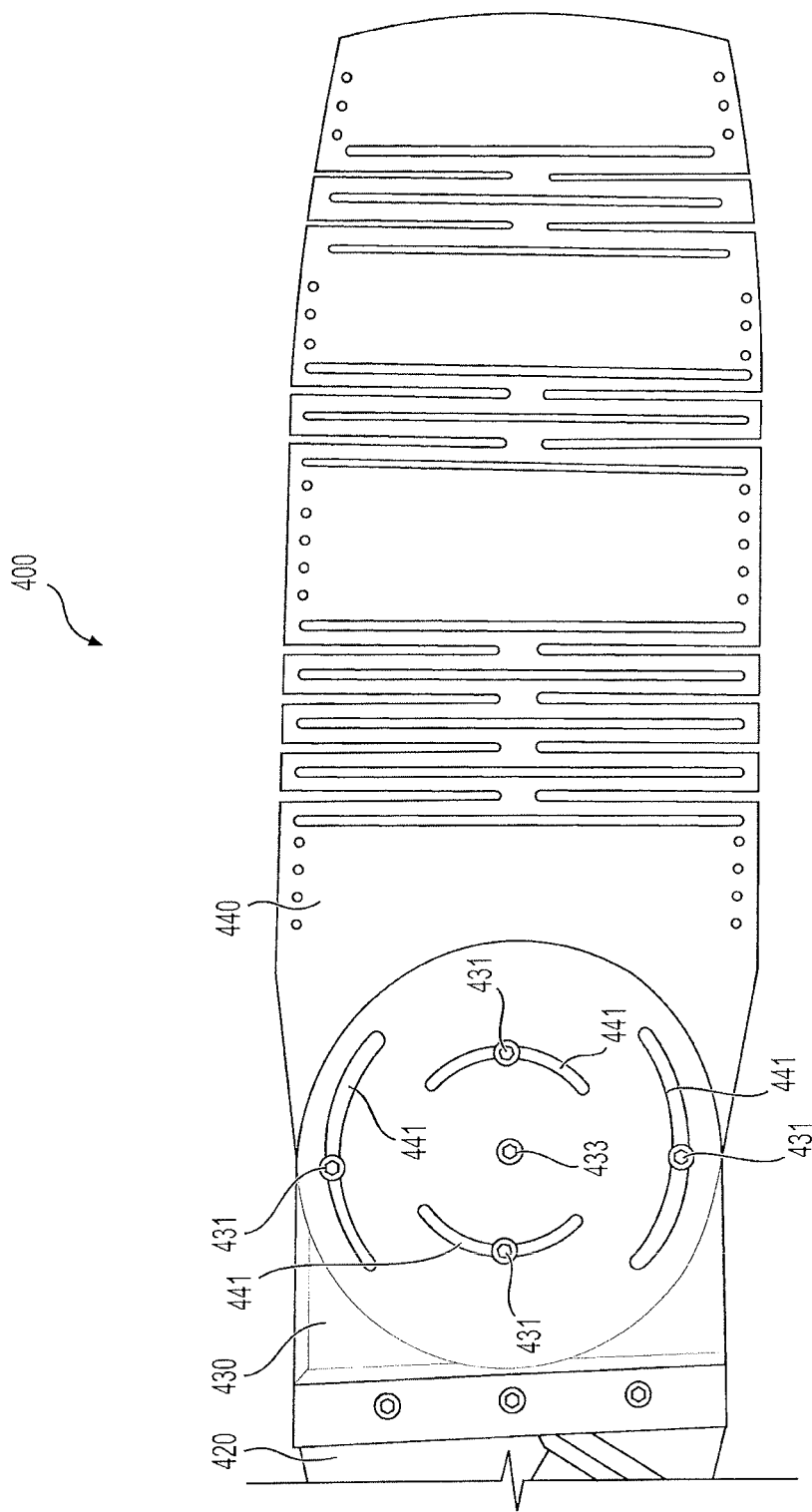
FIG. 23A is a top view of a fourth embodiment of a robotic gripping assist, shown in an aligned configuration.
Figure 23B:
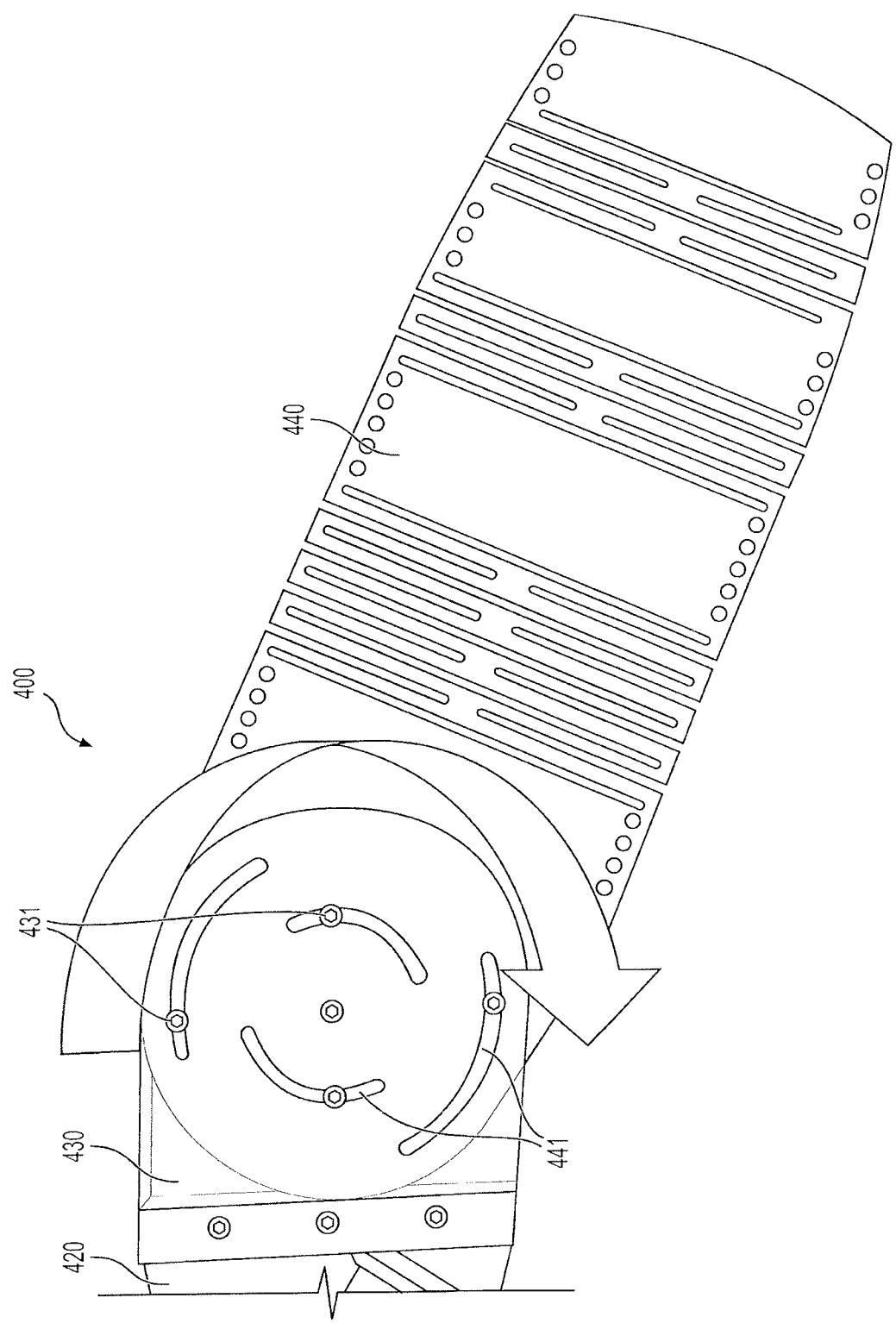
FIG. 23B is a top view of a fourth embodiment of a robotic gripping assist, shown in a pivoted configuration.
Figure 23C:
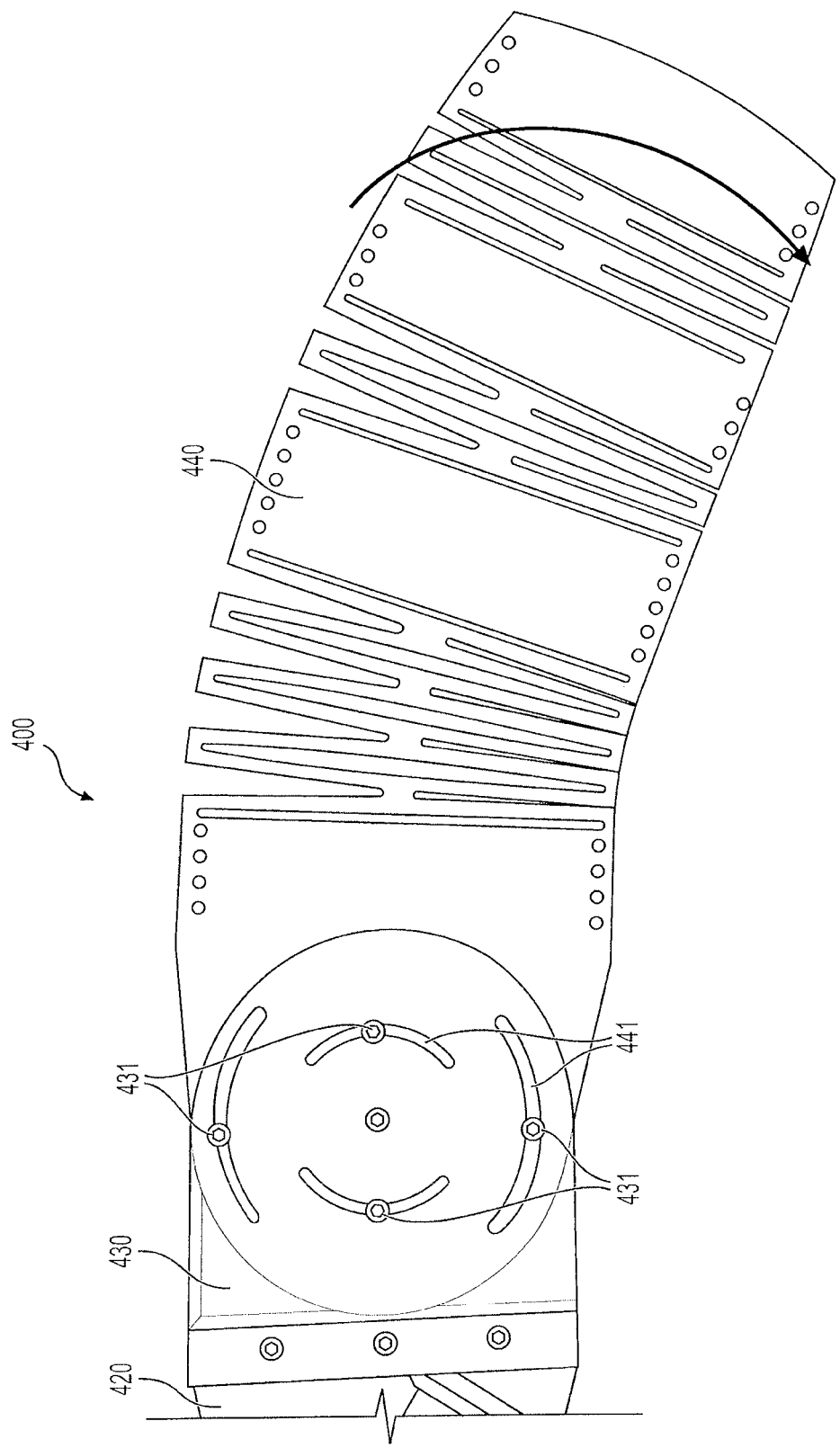
FIG. 23C is a top view of a fourth embodiment of a robotic gripping assist, shown in a flexed configuration.
Figure 23D:
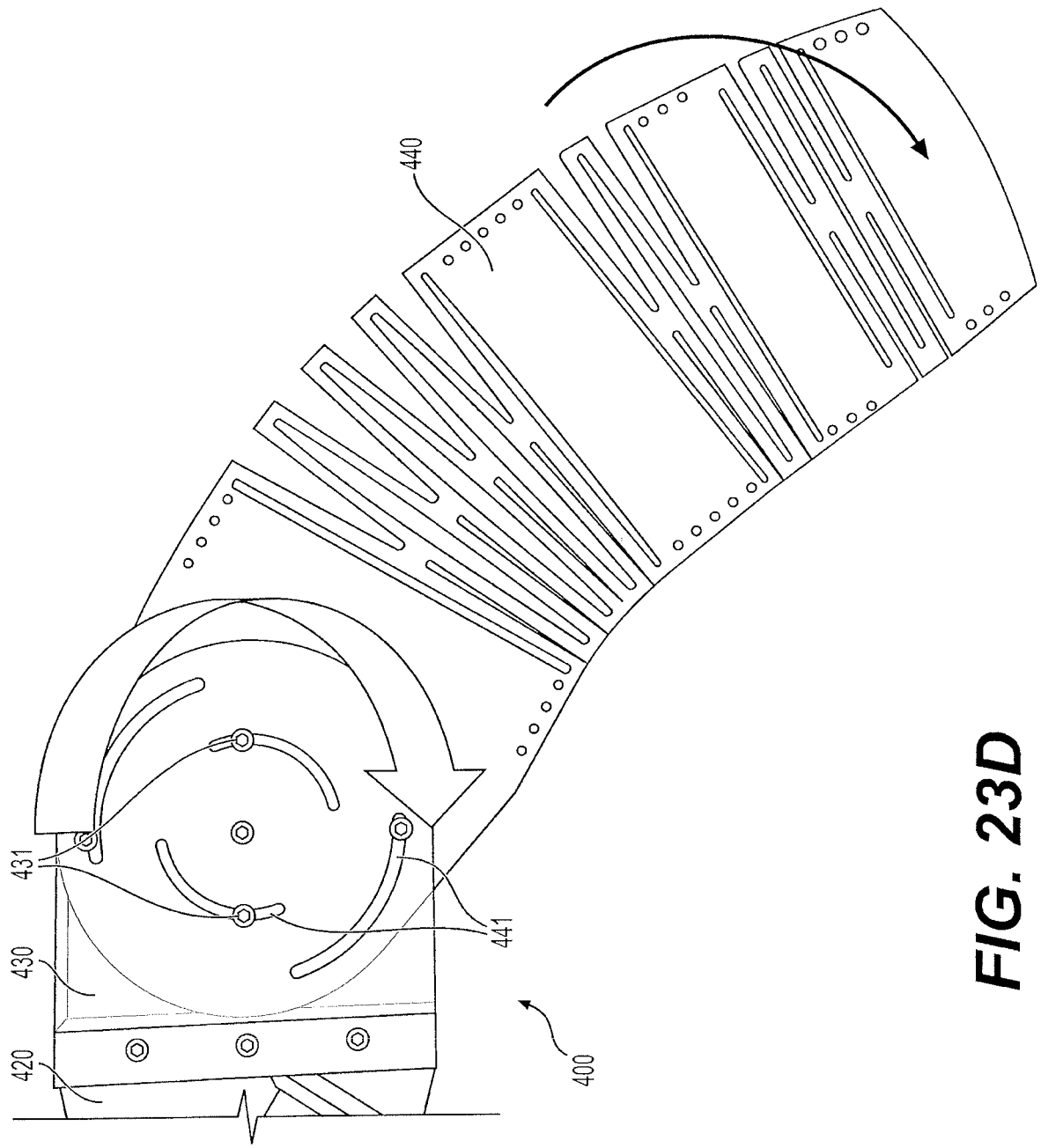
FIG. 23D is a top view of a fourth embodiment of a robotic gripping assist, shown in a flexed and pivoted configuration.

FIGS. 23A-23D show a flexible member 440, pivot plates 430, and a base member 420 of a fourth embodiment of the RGA 400. An upper pivot plate 430 is attached to an upper surface of the base member 420 and flexible member 440, and a lower pivot plate 430 is attached to a lower surface of the base member 420 and flexible member 440 (see FIG. 25A). A pivot portion of the flexible member 440 defines multiple arced slots 441 surrounding a central hole 433, the center point or central axis of each arc of the arced slots 441 being located at the central hole 433. Five bolts 431 extend from the upper pivot plate 430 to the lower pivot plate 430, one in each slot 441 and one in the central hole 433. A range of motion of the pivot is defined by the length of the slots 441. As seen in FIG. 23A, the bolts 431 are located at the center of the slots 442 when the flexible member 440 is aligned with the base member 420. FIG. 23B shows the flexible member 440 pivoted clockwise to the end of the range of motion, which is limited by the arced slots 441. The range of motion will be similar in the counterclockwise direction The range of motion can be adjusted be adjusting the length of the arced slots 441. In addition to pivoting with respect to the pivoting plates 430, the flexible member 440 may flex laterally. As seen in FIG. 23C, lateral wrist movement may be provided by flexion of the flexible member 440 alone. FIG. 23D shows the maximum lateral wrist flexion provided by both the pivot and flexion of the flexible member 440.

Figure 24A:
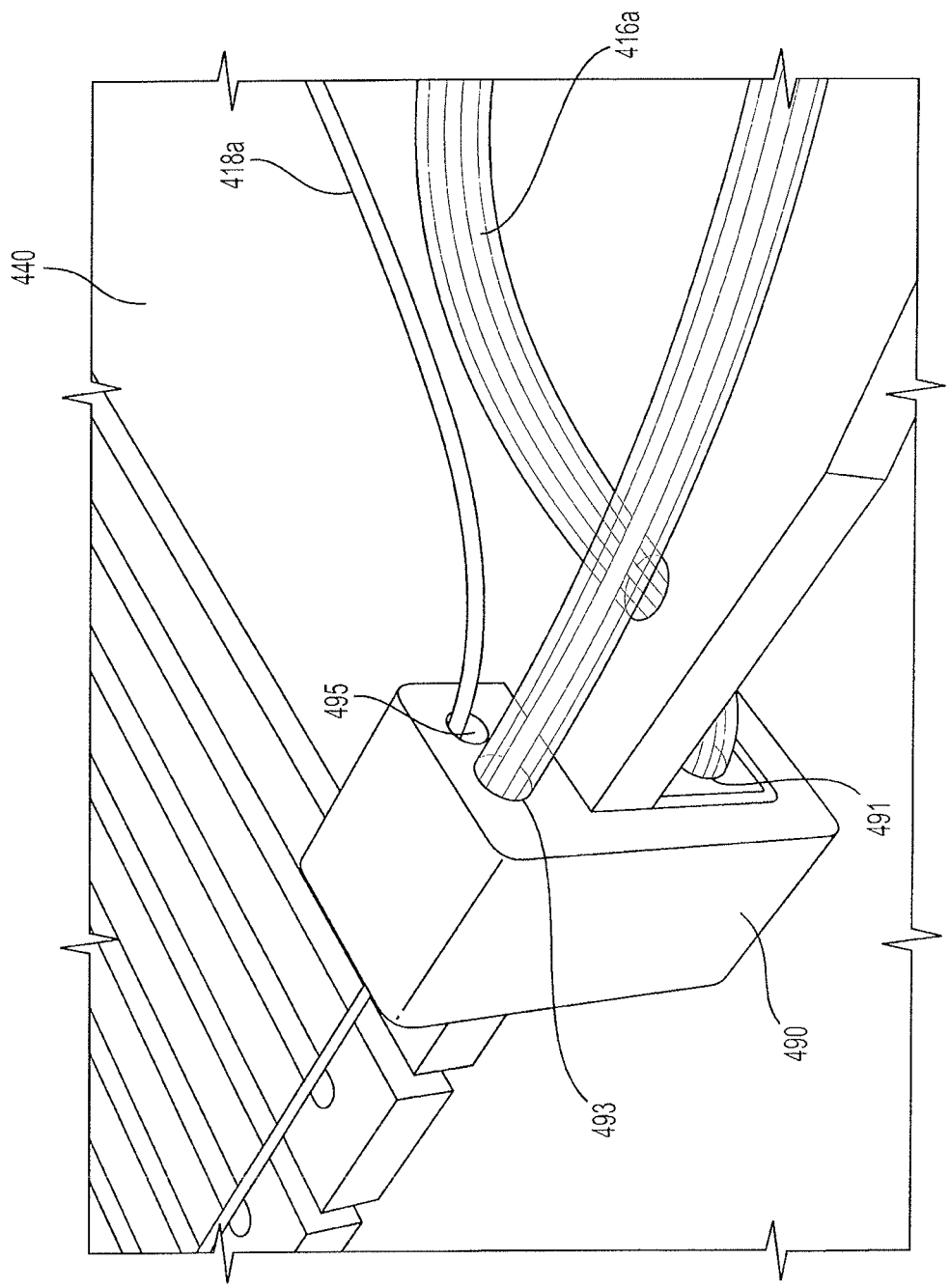
FIG. 24A is a partial perspective view of the fourth embodiment of a robotic gripping assist including a fifth embodiment of a clip.
Figure 24B:
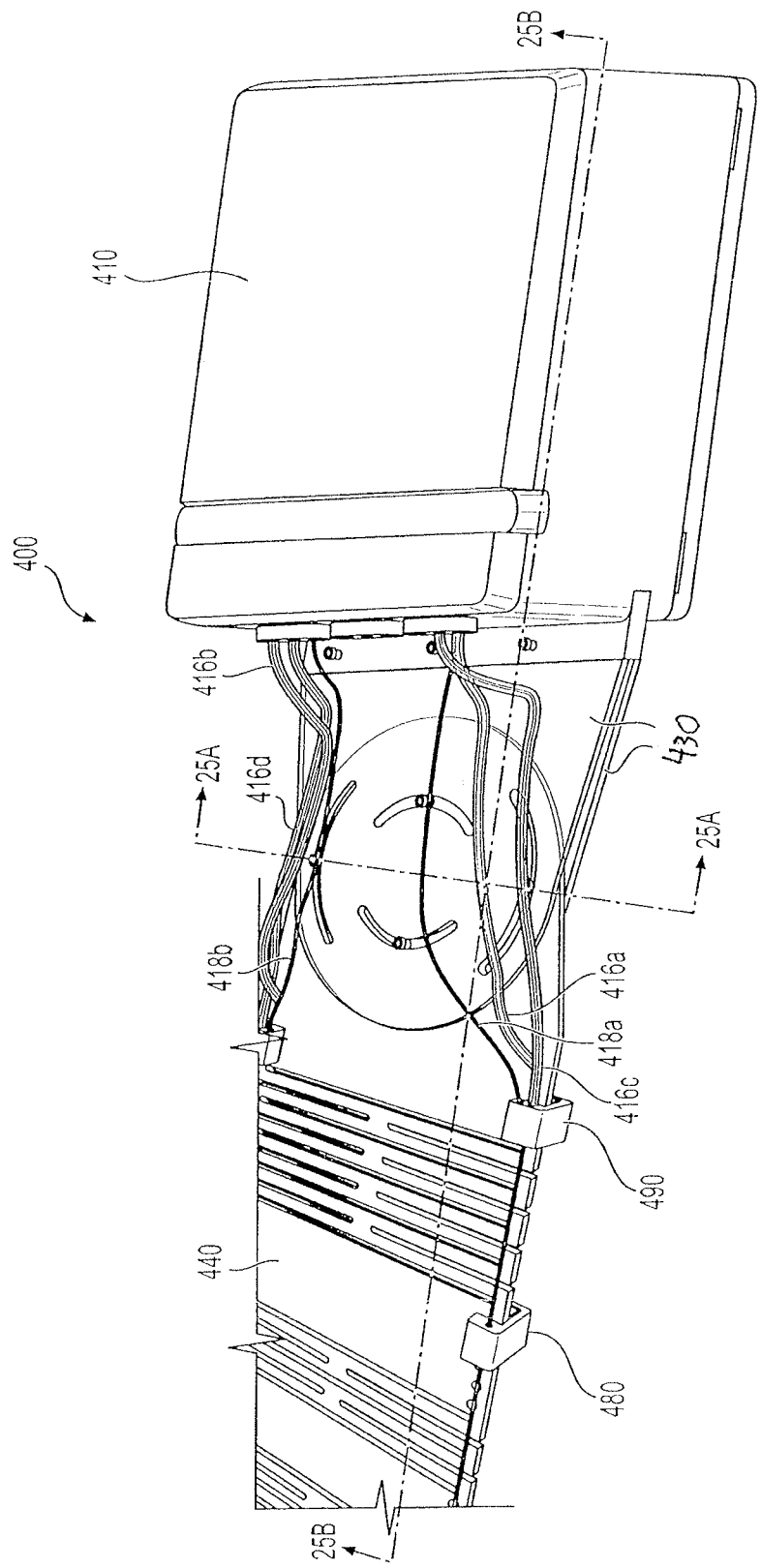
FIG. 24B is another partial perspective view of the fourth embodiment of a robotic gripping assist.

FIGS. 24A and 24B show the fourth embodiment of the RGA 400 with attached wires 216*a*-416*d*, 418*a*, 418*b*. The fourth embodiment may include both the upper 416*a*, 416*b* and lower 416*c*, 416*d* wires as discussed with regard to the previous embodiments for moving the flexible member 440 to a gripping or non-gripping position. In addition, the RGA 400 may include two pivoting wires 418*a*, 418*b*. The pivoting wires 418*a*, 418*b* may extend to only the first clip 490 on the flexible member 440. As seen in FIG. 24A, the first clip 490 on each side of the flexible member 440 may include an anchoring hole 495, in addition to the upper and lower wire guides 491, 493. The anchoring hole 495 is located above the flexible member 440. The pivoting wires 418*a*, 418*b* may be anchored in the anchoring hole 495, or alternatively anchored to the first clip 490 using any means known in the art. The flexible member 440 may be pivoted to the left by reeling in the pivoting wire 418*a* connected to the clip 490. To provide additional leftward wrist flexion, the wires 416*a*, 416*c* for flexing the flexible member into gripping and non-gripping position on the left side may be reeled-in, while wires 416*b*, 416*d* on the opposing side are let out to bend the flexible member 440 to the left, thus resulting in the maximum leftward flexion, shown in FIG. 23D.

Figure 25A:
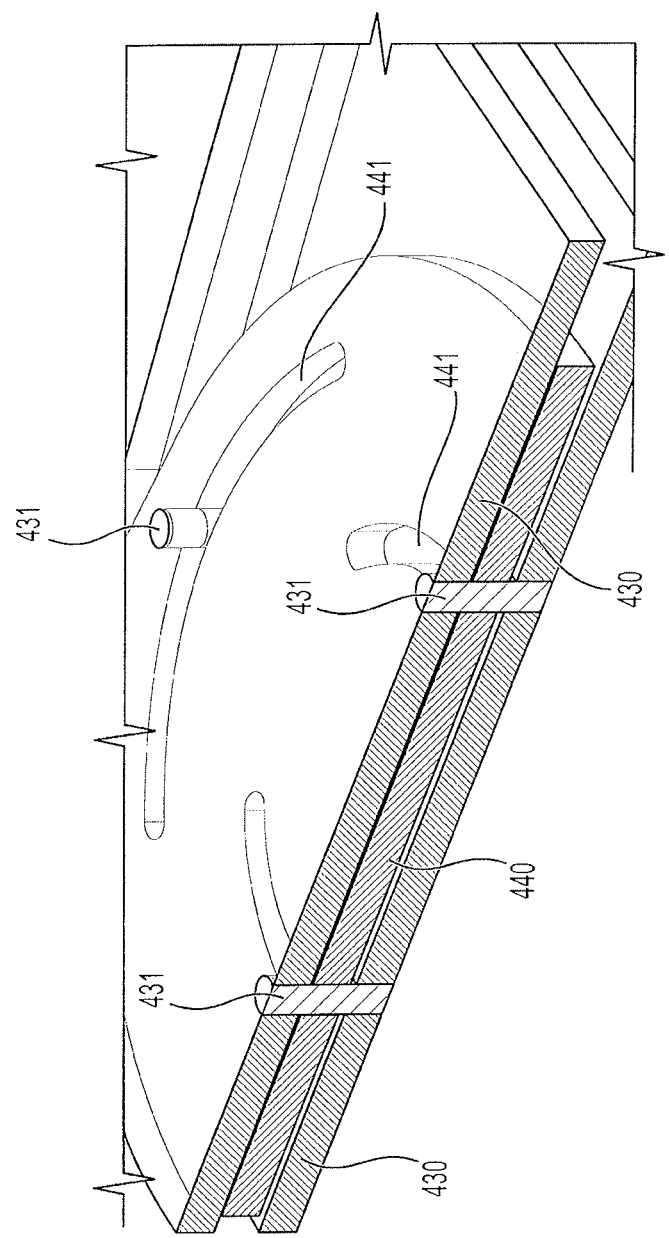
FIG. 25A is a section view drawn along lines 25A-25A of FIG. 24B.

FIG. 25A details the interaction between the flexible member 440 and the pivot plates 430. As seen in FIG. 25A, the pivot plates 430 sandwich the pivot portion of the flexible member 440. The bolts 431 extend through matching holes in both the upper and lower pivot plates 430 and through the arced grooves 441 in the flexible member 440. As previously discussed, the arced grooves 441 allow the flexible member 440 to be rotated with respect to the pivot plates 430, which are rigidly attached to the arm box 410. The embodiment shown in FIG. 25A does not include the central bolt 433 included in the embodiment shown in FIGS. 23A-23D.

Figure 25B:
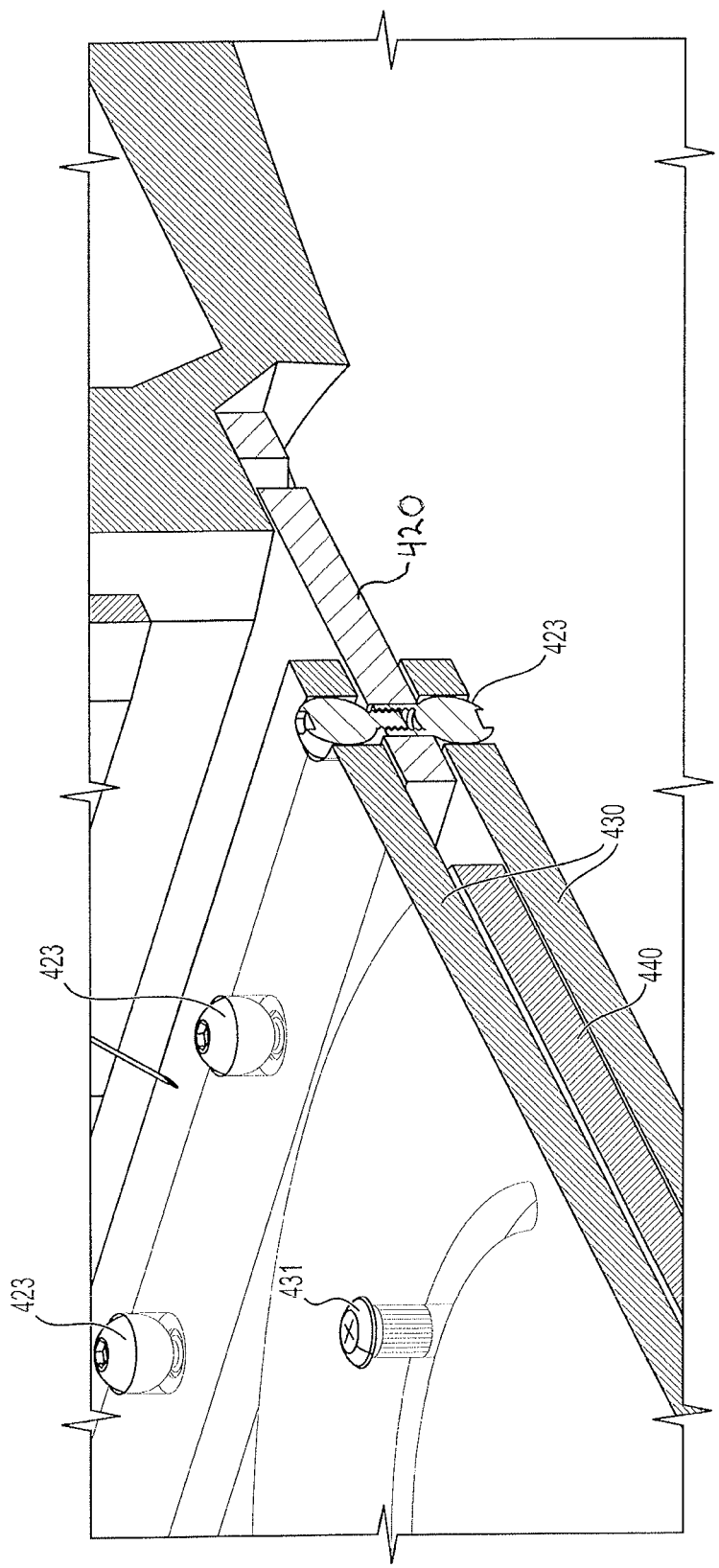
FIG. 25B is a section view drawn along lines 25B-25B of FIG. 24B.

FIG. 25B shows an embodiment of a connection between the pivot plates 430 and the base member 420. Blind screws 431 may be used to clamp the pivot plates 430 together with the flexible member 440 disposed between the pivot plates. Since the blind screws 431 are clamping the pivot plates 430 together and retaining the flexible member 440, ball head screws 423 may be used to secure the base member 420 between the pivot plates 430.

In some embodiments, each wire on the RGA 100, 200, 300, or 400 may have a respective motor and spool. For example, with regard to the RGA 400 having the pivotal flexible member 440, each of the gripping and non-gripping wires 416*a*-416*d* may have their own motor and each of the pivoting wires 418*a*, 418*b* may have their own motor, resulting in six separate motors. Individual motors provide for individual operation of each wire. For example, if a user would like to flex their wrist to the right, the three motors operating the wires 416*b*, 416*d*, 418*b* on the right side may reel in their wires 416*b*, 416*d*, 418*b*, while the three motors operating the wires 416*a*, 416*c*, 418*a* on the left side may let out their wires 416*b*, 416*d*, 418*b*. Alternatively, in scenarios where different portions of a user's hand have different strengths, the motors can operate at different forces to equalize the overall gripping force. For example, if the fingers on the right side of the user's hand are weaker than the left, the motor controlling the gripping wire 416*b* on the right can provide more force than the left, or only the motor controlling the wire 416*b* on the right can operate when gripping. In some embodiments, a single motor may be connected to a gear box, which provides for simultaneous, individual operation of each wire. In some embodiments, the motors may be synchronized and calibrated to work together.

The RGA 100, 200, 300, and 400 may be controlled using various methods, which may depend on the scenario or user preference. In some embodiments, movement of the bending member 40, 50 or the flexible member 340, 440 may be controlled by myoelectric signals from the user. For example, a surface electromyography (EMG) sensor for indicating flexion of the fingers, moving the flexible member 340 into a gripping position, may be installed on the user's flexor carpum radialis. The flexor carpum radialis is the muscle that primarily powers the gripping motion. Therefore, the device will work simultaneously with the muscle, based on the user's brain input. Similarly, the surface EMG sensor for indicating extension for the fingers, moving the bending member 40, 50 or the flexible member 340, 440 to the straight position, may be placed on the ipsilateral forearm extensors, which provide power for straightening the fingers.

Alternately, operation of the RGA 100, 200, 300, and 400 may be controlled by pressure pads or sensors. For example, a pressure pad may be installed on the palm or fingers of the mitten 70. When the pressure pad senses a preset amount of pressure, the RGA 100, 200, 300, and 400 will move the bending member 40, 50 or flexible member 340, 440 to the gripping position for gripping an object. The object may be released by a second pressure sensor or switch that can be used for moving the bending member 40, 50 of flexible member 340, 440 to a straight position. Force pads or sensors may be used in place of the pressure sensors.

In cases where the user's medical condition limits use of only one hand, a remote switch or button may be used to control operation of the RGA 100, 200, 300, 400. The switch/button may be held in the user's properly functioning hand, and the functioning hand can be used to operate the button, and therefore the RGA 100, 200, 300, 400. This setup may be beneficial when the RGA 100, 200, 300, 400 is being used as a rehabilitation tool. The above controller embodiments may be used with all embodiments of the RGA 100, 200, 300, 400.

It is to be understood that the robotic gripping assist is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A robotic gripping assist for assisting a person having a hand with weakened hand grip, comprising:
    an elongated flexible member having opposed first and second sides, the flexible member being adapted for overlying a dorsal aspect of the hand having the weakened hand grip, the flexible member having a plurality of flexible portions and a plurality of rigid portions, the flexible portions and the rigid portions alternating the length of the flexible member, wherein the flexible member has, in sequence, at least a first rigid portion followed by a first flexible portion, a second rigid portion followed by a second flexible portion, the first rigid portion is positioned to align with and extend over a person's metacarpal bone to the metacarpophangeal joint, further wherein the rigid portions comprise sheets having apertures defined therein adjacent the first and second edges of the rigid portions, and the flexible portions having alternating enclosed slots and open slots, the open slots defining opposing gaps in the first and second sides of the flexible portion;
    a first plurality of clips attached to the first side of the rigid portions and a second plurality of clips attached to the second side of the rigid portions, each of the clips having an upper end and a lower end, the lower ends of the clips extending below the sides of the rigid portions, wherein each of the clips defines an upper peg and a lower peg, the upper and lower pegs residing within the clip apertures of the rigid portions when the clip is connected thereto thereby engaging the opposed first and second sides;
    a first lower wire threaded through the lower end of the clips on the first side of the rigid portions, the first lower wire connecting the lower ends of the first plurality of clips in series;
    a second lower wire threaded through the lower end of the clips on the second side of the rigid portions, the second lower wire connecting the lower ends of the second plurality of clips in series;
    at least one spool, the first and second lower wires being mounted on the at least one spool; and
    at least one motor having a shaft connected to the at least one spool;
    wherein actuation of the at least one motor for rotation in a first direction pulls in the lower wires to flex the flexible member downward to flex the hand having the weakened hand grip to assist gripping the object, and actuation of the at least one motor for rotation in a second direction lets out the lower wires to assist in releasing the grip of the weakened hand on the object.

2. The robotic gripping assist of claim 1, further comprising a first upper wire and a second upper wire, the first and second upper wires being mounted on said at least one spool, the first upper wire being threaded through the upper end of the first plurality of clips and connecting the first plurality of clips in series, the second upper wire being threaded through the upper end of the second plurality of clips and connecting the second plurality of clips in series, wherein actuation of the motor for rotation in a first direction pulls in the lower wires and lets out the upper wires to flex the flexible member downward to flex the hand having the weakened hand grip to assist gripping the object, and actuation of the motor for rotation in a second direction pulls in the upper wires and let out the lower wires to extend the hand having the weakened hand grip to assist in releasing the grip on the object.

3. The robotic gripping assist of claim 2, wherein the upper wires and the lower wires are wound around the at least one spool in opposite directions.

4. The robotic gripping assist according to claim 2, wherein:
    said at least one motor comprises a first motor and a second motor;
    said at least one spool comprises a first spool connected to the shaft on the first motor and a second spool connected to the shaft of the second motor, the first motor actuating the upper and lower wires on the first side of the flexible member and the second motor actuating the upper and lower wires on the second side of the flexible member.

5. The robotic gripping assist of claim 2, further comprising further comprising an arm box adapted for being supported on a forearm of the person having a hand with weakened hand grip, the arm box housing the at least one motor and the at least one spool, the flexible member having a proximal end attached to the arm box and a distal end adapted for overlying a dorsal aspect of the hand having the weakened hand grip.

6. The robotic gripping assist according to claim 5, further comprising:
 a pair of spaced apart pivot plates extending from said arm box, the proximal end of said flexible member being pivotally disposed between the pair of pivot plates; and
 a central pivot pin extending between the pair of pivot plates and through the proximal end of said flexible member;
 whereby said flexible member may pivot clockwise and counterclockwise to rehabilitate a wrist of the person having a hand with weakened hand grip.

7. The robotic gripping assist according to claim 6, wherein said pair of pivot plates and the proximal end of said flexible member have a plurality of aligned arcuate slots defined therein, the robotic gripping assist further comprising corresponding guide fasteners extending through the aligned arcuate slots and being fastened to said pivot plates, whereby pivoting of said flexible member is limited by said arcuate slots.

8. The robotic gripping assist according to claim 7, further comprising a first pivot actuator wire attached to one of the first plurality of clips adjacent the proximal end of said flexible member and a first pivot actuator wire attached to one of the first plurality of clips adjacent the proximal end of said flexible member.

9. The robotic gripping assist according to claim 8, wherein:
 said at least one motor comprises a first pivot actuator motor and a second pivot actuator motor;
 said at least one spool comprises a first pivot wire spool connected to the shaft of the first pivot actuator motor and a second pivot wire spool connected to the shaft of the second pivot actuator motor, the first and second pivot actuator wires being mounted on the first and second pivot wire spool, respectively; and
 the first pivot actuator motor and the second pivot actuator motor are actuated so that the motors pull in one of the pivot actuator wires while simultaneously letting out the other pivot actuator wire to pivot said flexible member clockwise or counterclockwise.

10. The robotic gripping assist of claim 1, wherein said flexible member has, in sequence, a third rigid portion followed by a third flexible portion, and a fourth rigid portion.

11. The robotic gripping assist of claim 10, wherein the first flexible portion is positioned to align with to the metacarpophalangeal joint of the hand of the person, the second flexible portion is positioned to align with proximal interphalangeal joint of the hand of the person, and the third flexible portion is positioned to align with the distal interphalangeal joint of the hand of the person.

12. The robotic gripping assist of claim 1, wherein the clips are attached to the flexible member via a snap-fit connection.

* * * * *